(12) United States Patent
Stock et al.

(10) Patent No.: US 7,794,965 B2
(45) Date of Patent: Sep. 14, 2010

(54) METHOD OF IDENTIFYING MODULATORS OF PP2A METHYLASE

(75) Inventors: Gregory Stock, Los Angeles, CA (US); Jeffry B. Stock, Rocky Hill, NJ (US); Maxwell Stock, Rocky Hill, NJ (US); Scott Vafai, Boston, MA (US)

(73) Assignees: Signum Biosciences, Inc., Monmouth Junction, NJ (US); The Trustees of Princeton University, Princeton, NJ (US)

( * ) Notice: Subject to any disclaimer, the term of this patent is extended or adjusted under 35 U.S.C. 154(b) by 497 days.

(21) Appl. No.: 10/579,369

(22) PCT Filed: Mar. 13, 2003

(86) PCT No.: PCT/US03/07658

§ 371 (c)(1),
(2), (4) Date: May 15, 2006

(87) PCT Pub. No.: WO03/078448

PCT Pub. Date: Sep. 25, 2003

(65) Prior Publication Data

US 2007/0031909 A1 Feb. 8, 2007

Related U.S. Application Data

(60) Provisional application No. 60/363,537, filed on Mar. 13, 2002.

(51) Int. Cl.
*C12Q 1/42* (2006.01)
(52) U.S. Cl. .......................... 435/21; 435/69.2; 800/12
(58) Field of Classification Search .................. 435/21, 435/69.2; 800/12
See application file for complete search history.

(56) References Cited

U.S. PATENT DOCUMENTS

| | | | |
|---|---|---|---|
| 2,852,520 A | 9/1958 | Robinson | |
| 3,832,253 A | 8/1974 | DiPalma et al. | |
| 3,854,480 A | 12/1974 | Zaffaroni | |
| 4,105,027 A | 8/1978 | Lundquist | |
| 4,185,118 A | 1/1980 | Kathawala | |
| 4,192,309 A | 3/1980 | Poulsen | |
| 4,194,002 A | 3/1980 | Kathawala | |
| 4,201,785 A | 5/1980 | Kathawala | |
| 4,227,522 A | 10/1980 | Carris | |
| 4,229,463 A | 10/1980 | Kathawala | |
| 4,248,893 A | 2/1981 | Kathawala et al. | |
| 4,409,253 A | 10/1983 | Morrison, Jr. et al. | |
| 4,448,785 A | 5/1984 | Kathawala et al. | |
| 4,452,775 A | 6/1984 | Kent | |
| 4,627,432 A | 12/1986 | Newell et al. | |
| 4,658,063 A | 4/1987 | Tahara et al. | |
| 4,667,014 A | 5/1987 | Nestor, Jr. et al. | |
| 4,709,094 A | 11/1987 | Weber et al. | |
| 4,748,034 A | 5/1988 | de Rham | |
| 4,811,731 A | 3/1989 | Newell et al. | |
| 4,900,749 A | 2/1990 | Matsumoto et al. | |
| 4,906,779 A | 3/1990 | Weber et al. | |
| 4,933,324 A | 6/1990 | Shashoua | |
| 4,935,422 A | 6/1990 | Patil et al. | |
| 4,939,174 A | 7/1990 | Shashoua | |
| 4,977,170 A | 12/1990 | Matsumoto et al. | |
| 5,035,237 A | 7/1991 | Newell et al. | |
| 5,075,109 A | 12/1991 | Tice et al. | |
| 5,093,525 A | 3/1992 | Weber et al. | |
| 5,175,183 A | 12/1992 | Brooks et al. | |
| 5,189,049 A | 2/1993 | Frehel et al. | |
| 5,190,976 A | 3/1993 | Weber et al. | |
| 5,239,660 A | 8/1993 | Ooi | |

(Continued)

FOREIGN PATENT DOCUMENTS

AU 64586 12/1994

(Continued)

OTHER PUBLICATIONS

Lee J. et al. A Specific Protein Carboxyl Methylesterase . . . PNAS 93(12)6043-6047, 1996.*

(Continued)

*Primary Examiner*—Ralph Gitomer
(74) *Attorney, Agent, or Firm*—Choate Hall & Stewart LLP; Brenda Herschbach Jarrell; Katherine Nicole Clouse

(57) ABSTRACT

The invention relates to methylated proteins that control protein phosphorylation, particularly phosphoesterases, such as PP2A. It relates to screening methods for determining agents that affect methylation of these proteins and thus also modulate the level of phosphorylation of phosphoproteins. It relates as well to the agents and to compositions comprising the agents. In a particular aspect in this regard the invention relates to agents that alter PP2A methylation and that thereby affect phosphorylation of phosphoproteins that play an important role in health or disease, such as the tau protein which is implicated in the etiology of Alzheimer's Disease. The invention further relates to diagnostic methods based on protein methylation levels, to compositions comprising agents for affecting methylation of proteins and for controlling the phosphate complement of phosphoproteins. Additionally, the invention relates to methods for administering the agents and compositions to affect methylation of proteins physiologically and to modulate the phosphate complement of phosphoproteins. Examples in this regard include agents and compositions that affect physiological activity of PP2A and alter the phosphate complement of phosphoproteins that are altered in disease.

81 Claims, 2 Drawing Sheets

U.S. PATENT DOCUMENTS

| | | |
|---|---|---|
| 5,284,876 A | 2/1994 | Shashoua et al. |
| 5,322,858 A | 6/1994 | Canfield et al. |
| 5,502,056 A | 3/1996 | Breitbarth |
| 5,527,811 A | 6/1996 | Natsugari et al. |
| 5,565,491 A | 10/1996 | Schieven |
| 5,585,358 A | 12/1996 | Bialer et al. |
| 5,585,513 A | 12/1996 | Matthews et al. |
| 5,668,180 A | 9/1997 | Lesieur et al. |
| 5,670,499 A | 9/1997 | Cho et al. |
| 5,684,033 A | 11/1997 | Cho et al. |
| 5,693,627 A | 12/1997 | Schieven |
| 5,700,821 A | 12/1997 | Lazo et al. |
| 5,714,094 A | 2/1998 | Bertholet et al. |
| 5,777,162 A | 7/1998 | Matthews et al. |
| 5,795,877 A | 8/1998 | Jackson et al. |
| 5,821,261 A | 10/1998 | Durette et al. |
| 5,824,662 A | 10/1998 | Slusher et al. |
| 5,849,764 A | 12/1998 | Goulet et al. |
| 5,856,506 A | 1/1999 | Lazo et al. |
| 5,863,536 A | 1/1999 | Jackson et al. |
| 5,880,132 A | 3/1999 | Hill |
| 5,902,817 A | 5/1999 | Jackson et al. |
| 5,914,242 A | 6/1999 | Honkanen et al. |
| 5,925,660 A | 7/1999 | Lazo et al. |
| 5,939,563 A | 8/1999 | Matthews |
| 5,962,521 A | 10/1999 | Jackson et al. |
| 5,977,090 A | 11/1999 | Slusher et al. |
| 5,981,526 A | 11/1999 | Hargreaves |
| 5,985,855 A | 11/1999 | Slusher et al. |
| 5,994,392 A | 11/1999 | Shashoua |
| 6,004,946 A | 12/1999 | Slusher et al. |
| 6,013,658 A | 1/2000 | Lau et al. |
| 6,017,903 A | 1/2000 | Slusher et al. |
| 6,025,344 A | 2/2000 | Jackson et al. |
| 6,040,323 A | 3/2000 | Lazo et al. |
| 6,046,180 A | 4/2000 | Jackson et al. |
| 6,048,868 A | 4/2000 | Fourtillan et al. |
| 6,054,444 A | 4/2000 | Jackson et al. |
| 6,071,965 A | 6/2000 | Jackson et al. |
| 6,107,499 A | 8/2000 | Shashoua |
| 6,132,973 A | 10/2000 | Lal et al. |
| 6,140,324 A | 10/2000 | Tattersall |
| 6,159,704 A | 12/2000 | Hemmings |
| 6,180,624 B1 | 1/2001 | Hill |
| 6,200,768 B1 * | 3/2001 | Mandelkow et al. .......... 435/15 |
| 6,232,110 B1 | 5/2001 | Pallas et al. |
| 6,271,245 B1 | 8/2001 | Jackson et al. |
| 6,277,566 B1 * | 8/2001 | Beachy et al. .................. 435/6 |
| 6,288,046 B1 | 9/2001 | Jackson et al. |
| 6,300,363 B1 | 10/2001 | Stevens et al. |
| 6,303,610 B1 | 10/2001 | Johnson et al. |
| 6,306,912 B1 | 10/2001 | Mueller et al. |
| 6,337,344 B1 | 1/2002 | Defossa et al. |
| 6,350,767 B1 | 2/2002 | Lau et al. |
| 6,353,015 B1 | 3/2002 | Oxenkrug et al. |
| 6,372,752 B1 | 4/2002 | Staveski et al. |
| 6,376,205 B1 | 4/2002 | Wischik et al. |
| 6,399,796 B2 | 6/2002 | Schwartz |
| 6,403,577 B1 | 6/2002 | Cho et al. |
| 6,451,468 B1 | 9/2002 | Adachi |
| 6,458,392 B1 | 10/2002 | Okawa et al. |
| 6,462,086 B1 | 10/2002 | Kloog et al. |
| 6,465,457 B1 | 10/2002 | Matthews et al. |
| 6,492,128 B1 | 12/2002 | Haklai et al. |
| 6,503,949 B1 | 1/2003 | Lau et al. |
| 6,528,295 B2 | 3/2003 | Pallas et al. |
| 6,528,655 B1 | 3/2003 | N'Zemba et al. |
| 6,541,468 B1 * | 4/2003 | Roder et al. ................. 514/219 |
| 6,551,816 B1 | 4/2003 | Bontoux et al. |
| 6,562,807 B2 | 5/2003 | Jorgensen et al. |
| 6,608,196 B2 | 8/2003 | Wang et al. |
| 6,653,304 B2 | 11/2003 | Leftheris et al. |
| 6,669,979 B1 | 12/2003 | Zhao et al. |
| 6,683,055 B1 | 1/2004 | Hillen et al. |
| 6,727,255 B1 | 4/2004 | Cho et al. |
| 6,750,359 B1 | 6/2004 | Copeland et al. |
| 6,760,359 B2 | 7/2004 | Evans |
| 6,818,655 B2 | 11/2004 | Dhanak et al. |
| 6,852,734 B2 | 2/2005 | Yamamoto et al. |
| 6,869,957 B1 | 3/2005 | Cho et al. |
| 6,869,975 B2 | 3/2005 | Abe et al. |
| 6,875,760 B2 | 4/2005 | Lau et al. |
| 6,921,527 B2 | 7/2005 | Platz et al. |
| 6,946,485 B2 | 9/2005 | Kloog et al. |
| 6,953,812 B2 | 10/2005 | Jorgensen et al. |
| 7,019,008 B2 | 3/2006 | Dhanak et al. |
| 7,041,702 B1 | 5/2006 | Durant et al. |
| 7,115,634 B2 | 10/2006 | Thurieau et al. |
| 7,157,456 B2 | 1/2007 | Straub et al. |
| 7,166,637 B2 | 1/2007 | Hofgen et al. |
| 7,173,027 B2 | 2/2007 | Makriyannis et al. |
| 7,241,923 B2 | 7/2007 | Fagerhad et al. |
| 7,282,593 B2 | 10/2007 | Nair et al. |
| 7,358,248 B2 | 4/2008 | Whitehouse et al. |
| 7,393,861 B2 | 7/2008 | Thurieau et al. |
| 7,459,472 B2 | 12/2008 | Mjalli et al. |
| 7,476,399 B2 | 1/2009 | Tachdjian et al. |
| 2001/0044459 A1 | 11/2001 | Jackson et al. |
| 2001/0056116 A1 | 12/2001 | Shashoua |
| 2002/0034524 A1 | 3/2002 | Poret |
| 2002/0107374 A1 | 8/2002 | Pallas et al. |
| 2002/0119972 A1 | 8/2002 | Leftheris et al. |
| 2002/0143186 A1 | 10/2002 | Jorgensen et al. |
| 2002/0160067 A1 | 10/2002 | Zapp et al. |
| 2003/0013846 A1 | 1/2003 | Wang et al. |
| 2003/0036070 A1 | 2/2003 | Chakravarti |
| 2003/0050226 A1 | 3/2003 | Shashoua |
| 2003/0100750 A1 | 5/2003 | Wang et al. |
| 2003/0149108 A1 | 8/2003 | Abe et al. |
| 2003/0153610 A1 | 8/2003 | Straub et al. |
| 2003/0171411 A1 | 9/2003 | Kodra et al. |
| 2003/0186416 A1 | 10/2003 | Pallas et al. |
| 2003/0215456 A1 | 11/2003 | Yao et al. |
| 2003/0220350 A1 | 11/2003 | Lau et al. |
| 2004/0006089 A1 | 1/2004 | Thurieau et al. |
| 2004/0022822 A1 | 2/2004 | Poret |
| 2004/0024045 A1 | 2/2004 | Jorgensen et al. |
| 2004/0053963 A1 | 3/2004 | Dhanak et al. |
| 2004/0058963 A1 | 3/2004 | Yamamoto et al. |
| 2004/0063757 A1 | 4/2004 | Dhanak et al. |
| 2004/0077851 A1 | 4/2004 | Makriyannis et al. |
| 2004/0096547 A1 | 5/2004 | Ferruzzi |
| 2004/0138224 A1 | 7/2004 | Dhanak et al. |
| 2004/0138238 A1 | 7/2004 | Dhanoa et al. |
| 2004/0147759 A1 | 7/2004 | Hofgen et al. |
| 2004/0152692 A1 | 8/2004 | Dhanak et al. |
| 2004/0176444 A1 | 9/2004 | Fagerhad et al. |
| 2004/0209934 A1 | 10/2004 | McCluskey et al. |
| 2004/0242655 A1 | 12/2004 | Anziano |
| 2004/0253356 A1 | 12/2004 | Fields |
| 2004/0266789 A1 | 12/2004 | Whitehouse et al. |
| 2004/0266822 A1 | 12/2004 | Wang et al. |
| 2005/0031761 A1 | 2/2005 | Brucker et al. |
| 2005/0043292 A1 | 2/2005 | Parker et al. |
| 2005/0043388 A1 | 2/2005 | Bombrun et al. |
| 2005/0049310 A1 | 3/2005 | Mjalli et al. |
| 2005/0059713 A1 | 3/2005 | Mjalli et al. |
| 2005/0059727 A1 | 3/2005 | Nair et al. |
| 2005/0074831 A1 | 4/2005 | Jerecic et al. |
| 2005/0084506 A1 | 4/2005 | Tachdjian et al. |
| 2005/0129827 A1 | 6/2005 | Miljkovic et al. |
| 2005/0181041 A1 | 8/2005 | Goldman |
| 2005/0197345 A1 | 9/2005 | Dhanak et al. |
| 2005/0203108 A1 | 9/2005 | Lau et al. |

| | | | | | | |
|---|---|---|---|---|---|---|
| 2005/0239796 | A1 | 10/2005 | Thurieau et al. | JP | 09301954 | 11/1997 |
| 2005/0245547 | A1 | 11/2005 | Kim et al. | JP | 10077229 | 3/1998 |
| 2005/0250819 | A1 | 11/2005 | Li et al. | JP | 10077267 | 3/1998 |
| 2005/0250839 | A1 | 11/2005 | Marnett et al. | JP | 2000-37188 | 2/2000 |
| 2005/0261197 | A1 | 11/2005 | Aoki | JP | 2000037188 A | 2/2000 |
| 2005/0261332 | A1 | 11/2005 | Distefano et al. | JP | 2001247539 | 9/2001 |
| 2006/0045953 | A1 | 3/2006 | Tachdjian et al. | JP | 2002193923 | 7/2002 |
| 2006/0063789 | A1 | 3/2006 | Freyne et al. | JP | 2002255837 A | 9/2002 |
| 2006/0159773 | A1 | 7/2006 | Holt | JP | 2003137780 | 5/2003 |
| 2006/0160109 | A1 | 7/2006 | MacDonald et al. | JP | 2004292383 | 10/2004 |
| 2006/0171938 | A1* | 8/2006 | Stock et al. ............ 424/94.6 | JP | 2007145763 | 6/2007 |
| 2006/0178378 | A1 | 8/2006 | Dai et al. | JP | 2008151366 A | 7/2008 |
| 2006/0199806 | A1 | 9/2006 | Failli et al. | JP | 2008207466 | 9/2008 |
| 2006/0223842 | A1 | 10/2006 | Moriconi et al. | JP | 2009001564 | 1/2009 |
| 2006/0258724 | A1 | 11/2006 | Straub et al. | KR | 2003038383 | 10/2002 |
| 2006/0270741 | A1 | 11/2006 | Durant et al. | KR | 2003038329 | 11/2003 |
| 2006/0293362 | A1 | 12/2006 | Norbert et al. | SU | 357508 | 10/1972 |
| 2007/0031909 | A1 | 2/2007 | Stock et al. | WO | WO-9116038 | 10/1991 |
| 2007/0082907 | A1 | 4/2007 | Canada et al. | WO | WO-9222559 | 12/1992 |
| 2007/0088072 | A1 | 4/2007 | Di Marzo et al. | WO | WO-9206955 | 4/1993 |
| 2007/0093531 | A1 | 4/2007 | Hofgen et al. | WO | WO-9707117 | 2/1997 |
| 2007/0105940 | A1 | 5/2007 | Di Marzo et al. | WO | WO-9806695 | 2/1998 |
| 2007/0129424 | A1 | 6/2007 | Di Marzo et al. | WO | WO-9901103 | 1/1999 |
| 2007/0149514 | A1 | 6/2007 | Woltering et al. | WO | WO-9901118 | 1/1999 |
| 2007/0161644 | A1 | 7/2007 | Stockwell | WO | WO-9945926 | 9/1999 |
| 2007/0191357 | A1 | 8/2007 | Antel et al. | WO | WO-0116334 | 3/2001 |
| 2007/0197629 | A1 | 8/2007 | Somei et al. | WO | WO-0120995 | 3/2001 |
| 2007/0203209 | A1 | 8/2007 | Bartolini et al. | WO | WO-0121606 | 3/2001 |
| 2007/0212677 | A1 | 9/2007 | MacDonald et al. | WO | WO 01/57535 | 8/2001 |
| 2007/0225283 | A1 | 9/2007 | Hammock et al. | WO | WO-0157535 | 8/2001 |
| 2007/0238775 | A1 | 10/2007 | Ruah et al. | WO | WO-0241700 | 5/2002 |
| 2007/0243134 | A1 | 10/2007 | Makriyannis et al. | WO | WO-02060462 | 8/2002 |
| 2007/0259945 | A1 | 11/2007 | De Petrocellis et al. | WO | WO-02085397 | 10/2002 |
| 2007/0280918 | A1 | 12/2007 | Schwartz et al. | WO | WO-02102397 | 12/2002 |
| 2008/0021198 | A1 | 1/2008 | Shi et al. | WO | WO-03008632 | 1/2003 |
| 2008/0027099 | A1 | 1/2008 | Govek et al. | WO | WO-03078448 | 9/2003 |
| 2008/0027112 | A1 | 1/2008 | Govek et al. | WO | WO-2004002504 | 1/2004 |
| 2008/0039442 | A1 | 2/2008 | Blom et al. | WO | WO-2004031177 | 4/2004 |
| 2008/0090815 | A1 | 4/2008 | Straub et al. | WO | WO-2004063147 | 7/2004 |
| 2008/0161341 | A1 | 7/2008 | Calderwood et al. | WO | WO-2005009349 | 2/2005 |
| 2008/0161351 | A1 | 7/2008 | Abe et al. | WO | WO-2005037839 | 4/2005 |
| 2008/0176846 | A1 | 7/2008 | Chianelli et al. | WO | WO-2005071101 | 8/2005 |
| 2008/0176854 | A1 | 7/2008 | Quintana-Ruiz et al. | WO | WO-2005084664 | 9/2005 |
| 2008/0200473 | A1 | 8/2008 | Falco et al. | WO | WO-2005089502 | 9/2005 |
| 2008/0200674 | A1 | 8/2008 | Straub et al. | WO | WO-2006015258 | 2/2006 |
| 2008/0213406 | A1 | 9/2008 | Stock et al. | WO | WO-2006028226 | 3/2006 |
| 2008/0221197 | A1 | 9/2008 | Lam et al. | WO | WO-2006084033 | 8/2006 |
| 2008/0287516 | A1 | 11/2008 | Wu et al. | WO | WO-2006094235 | 9/2006 |
| 2009/0005430 | A1 | 1/2009 | Somei et al. | WO | WO-2006101456 | 9/2006 |
| 2009/0029355 | A1 | 1/2009 | Zhao et al. | WO | WO-2006104826 | 10/2006 |
| | | | | WO | WO-2006117549 | 11/2006 |

FOREIGN PATENT DOCUMENTS

| | | |
|---|---|---|
| AU | 690107 | 12/1994 |
| AU | 2006230674 | 11/2006 |
| CA | 2125236 | 12/1994 |
| CN | 1205175 | 1/1999 |
| CN | 1304396 | 7/2001 |
| CN | 1403137 A | 3/2003 |
| CN | 1415596 | 5/2003 |
| CN | 1687072 | 10/2005 |
| DE | 3105850 | 8/1982 |
| EP | 0693547 | 1/1996 |
| EP | 714968 | 6/1996 |
| FR | 1238756 A | 8/1960 |
| FR | 2827866 | 1/2003 |
| FR | 2827866 A1 | 1/2003 |
| FR | 2879601 | 6/2006 |
| JP | 3268073 | 11/1991 |
| JP | 4156825 | 5/1992 |
| JP | 06025276 | 2/1994 |
| JP | 07052542 | 2/1995 |
| JP | 3795093 | 6/1996 |

| | | |
|---|---|---|
| WO | WO-2007008514 | 1/2007 |
| WO | WO-2007015866 | 2/2007 |
| WO | WO-2007079930 | 7/2007 |
| WO | WO-2007140551 | 12/2007 |
| WO | WO-2008007123 | 1/2008 |
| WO | WO-2008019357 | 2/2008 |
| WO | WO-2008031509 | 3/2008 |
| WO | WO-2008060791 | 5/2008 |
| WO | WO-2008061781 | 5/2008 |
| WO | WO-2008110196 | 9/2008 |
| WO | WO-2008112525 | 9/2008 |
| WO | WO-2008113760 | 9/2008 |
| WO | WO-2008127387 | 10/2008 |
| WO | WO-2008141013 | 11/2008 |
| WO | WO-2008155666 | 12/2008 |
| WO | WO-2008155668 | 12/2008 |
| WO | WO-2009020596 | 2/2009 |

OTHER PUBLICATIONS

Scott B., "Protein Phosphatase 2A Methylation." *FEBS Letters* 518(1-3):1-4 (2002).

Floer M., "Carboxyl Methylation of Protein Phosphatase 2A from Xenopus Eggs is Stimulated by CAMP and Inhibited by Okadaic Acid." *Biochem and Biophysical Res Com.* 198(1):372-379 (1994).

Lee J., "A Specific Protein Carboxyl Methylesterase that Demethylates Phosphoprotein Phosphatase 2A in Bovine Brain." *Proc Natl Acad Sci USA* 93(12):6043-6047 (1996).

Wu J., "Carboxyl Methylation of the Phosphoprotein Phosphatase 2A Catalytic Subunit Promotes it Functional Association with Regulatory Subunits." *The EMBO Journal* 19(21):5672-5681 (2000).

Tolstykh T., "Carboxyl Methylation Regulates Phosphoprotein Phosphatase 2A by Controlling the Association of Regulatory B Subunits." *The EMBO Journal* 19(21):5682-5691 (2000).

Abolhassani et al., "Hyperosmolarity Causes Inflammation through the Methylation of Protein Phosphatase 2A," 2008, *Inflammation Research*, 57(9):419-429, ISSN: 1023-3830.

Acker et al., "Photometric determination of shell constituents in cocoa products," 1966, *Suesswaren (Hamburg)*, 15(10):622-4, 626-8.

Aggen et al., "The Design, Synthesis, and Biological Evaluation of Analogues of the Serine-threonine Protein Phosphatase 1 and 2A Selective Inhibitor Microcystin LA: Rational Modifications Imparting PPI Selectivity," 1999, *Bioorganic & Medicinal Chemistry*, 7(3):543-564, ISSN: 0968-0896.

Albaugh et al., "Determination of distance distribution from time domain fluorometry," 1989, *J of Physical Chemistry*, 93(24):8013-16.

Alonso et al., "Alzheimer's disease hyperphosphorylated tau sequesters normal tau into tangles of filaments and disassemles microtubules," 1996, *Nat Med*, 2(7):783-787.

Alonso et al., "Hyperphosphorylation induces self-assembly of τ into tangles of paired helical filaments / straight filaments," 2001, *Proc Natl Acad Sci U S A*, 98:6923-2928.

Alonso et al., "Protein Tyrosine Phosphatases in the Human Genome," 2004, *Cell*, 117:699-711.

Alonso et al., "Role of abnormally phosphorylated tau in the breakdown of microtubules in Alzheimer disease," 1994, *Proc Natl Acad Sci U S A*, 91:5562-5566.

Appendino et al., "First 'hybrid' ligands of vanilloid TRPV1 and cannabinoid CB2 receptors and non-polyunsaturated fatty acid-derived CB2-selective ligands," 2006, *FEBS Letters*, 580(2):568-574.

Arino et al., "Human liver phosphatase 2A: cDNA and amino acid sequence of two catalytic subunit isotypes," 1988, *Proc Nat'l. Acad Sci. USA*, 85:4252-4256.

Ascherio et al., "Prospective Study of Caffeine Consumption and Risk of Parkinson's Disease in Men and Women," 2001, *Ann Neurol*, 50:56-63.

Bai et al., "Huperzine A, A Potential therapeutic Agent for Treatment of Alzheimer's Disease," 2000, *Current Medicinal Chemistry*, 7:355-374.

Battini et al., "Determination of N-Alkanoyl-5-Hydroxytryptamines (C-5-HT) in Coffee Beans by Means of HPLC and TLC," 1989, *Annali di Chimica*, 79(7-8):369-377.

Baumann, et al., "Abnormal Alzheimer-like phosphorylation of tau-protein by cyclin-dependent kinases cdk2 and cdk5," 1993, *FEBS Letters*, 336(3):417-424.

Bialy et al., "Synthesis and Biological Evaluation of Cytostatin Analogues," 2003, *Chemical Communications*, 15:1872-1873, ISSN: 1359-7345.

Bialy et al., "Synthesis of the Protein Phosphatase 2A Inhibitor (4S,5S,6S,10S,11S,12S)—cytostatin," 2002, *Angewandte Chemie, International Edition*, 41(10):1748-1751, ISSN: 1433-7851.

Biernat et al., "Phosphorylation of Ser$^{262}$ Strongly Reduces Binding of Tau to Microtubules: Distinction between PHF-like Immunoreactivity and Microtubule Binding," 1993, *Neuron*, 11:153-163.

Billingsley et al., "Regulated phosphorylation and dephosphorylation of tau protein: effects on microtubule interaction, intracellular trafficking and neurodegeneration," 1997, *Biochem J.*, 323:577-91.

Blickenstaff et al., "Potential radioprotective agents-V. Melatonin analogs. Oral activity of p-aminopropiophenone and its ethylene ketal," 1994, *Bioorganic & Medicinal Chemistry* 2(10):1057-60.

Blickenstaff et al., "Potential radioprotective agents. 1. Homologs of melatonin," 1994, *J. of Pharmaceutical Sciences*, 83(2):216-18.

Blickenstaff et al., "Potential radioprotective agents. VI. Chalcones, benzophenones, acid hydrazides, nitro amines and chloro compounds. Radioprotection of murine intestinal stem cells," 1995, *Bioorganic & Medicinal Chemistry* 3(7):917-22.

Boger et al., "Total Synthesis of Fostriecin (CI-920)," 2001, *J. of the American Chemical Society*, 123(18):4161-4167, ISSN: 0002-7863.

Borsotto et al., "PP2A-By subunit and KCNQ2K$^+$ channels in bipolar disorder," 2007, *Pharmacogenomics J.*, 7:123-132.

Boushey et al., "A quantitative assessment of plasma homocysteine as a risk factor for vascular disease," 1995, *JAMA*, 274:1049-1057.

Bramblett, et al, "Abnormal Tau Phosphorylation at Ser$^{396}$ in alzheimer's Disease Receapitulates Development and Contributes to Reduced Microtubule Binding," 1993, *Neuron*, 10:1089-1099.

Breitner, John, "Inflammatory Processes and Antinflammatory Drugs in Alzheimer's Disease: A Current Appraisal," 1996, *Neurobiology of Aging*, 17(5):789-794.

Brookmeyer et al., "Forecasting the global burden of Alzheimer disease," 2007, *Alzheimer's and Dementia*, 3(3):186-191.

Bryant et al., "Methylated C-terminal Leucine Residue of PP2A Catalytic Subunit is Important for Binding of Regulatory B Subunit," 1999, *Biochemical Journal*, 339(2):241-246, ISSN: 0264-6021.

Buznikov et al., "5-Hydroxytryptamides and 3-hydroxytyramides of polyenoic fatty acids as a tool for studying the pre-nervous biogenic monoamines' functions," 2000, *Rossiiskii Fiziologicheskii Zhurnal imeni I. M. Sechenova*, 86(9):1093-1108 (English language abstract in Appendix A).

Buée et al., "Tau protein isoforms, phosphorylation and role in neurodegenerative disorders," 2000, *Brain Res. Rev.*, 33(1):95-130.

Caudill et al., "Intracellular S-Adenosylhomocysteine Concentrations Predict Gobal DNA Hypomethylation in Tissues of Methyl-Deficient Cystathionine β-Synthase Heterozygous Mice," 2001, American Society for Nutritional Sciences, 131:2811-2818.

Cavin et al., "Cafestol and kahweol, two coffee specific diterpenes with anticarcinogenic activity," 2002, *Food and Chemical Toxicology*, 40:1155-1163.

Ceulemans et al., "Functional Diversity of Protein Phosphatase-1, a Cellular Economizer and Reset Button," 2004, *Physiol. Rev.*, 84:1-39.

Chan et al., "Folate Deprivation Increases Tau Phosphorylation by Homocysteine-induced Calcium Influx and by Inhibition of Phosphatase Activity: Alleviation by S-adenosyl Methionine," 2008, *Brain Research*, 1199:133-137, ISSN: 0006-8993.

Chandra et al., "Incidence Alzheimer's disease ina rural community in India," 2001, *Neurology*, 57(6).

Chao et al., "Structure and Mechanism of the Phosphotyrosyl Phosphatase Activator," 2006, *Molecular Cell*, 23(4):535-546.

Chavez et al., "Tryptamine Derived Amides and Acetogenins from the Seeds of rollinia mucosa," 1999, *J. Of Natural Products*, 62(8):1119-1122.

Chen et al., "Cheritamine, a new N-fatty acyl tryptamine and other constituents from the stems of annona cherimola," 1999, *J. of the Chinese Chemical Society* (Taipei), 46(1):77-86.

Chen et al., "Comparison of Protein Phosphatase Inhibition Activities and Mouse Toxicities of Microcystins," 2006, *Toxicon*, 47(7):742-746, ISSN: 0041-0101.

Chen et al., "Improved Synthesis and Characterization of L-histidine Norcantharimide, a Novel Potent Protein Phosphatase 2A Inhibitor," 2008, *J. of Chinese Pharmaceutical Sciences*, 17(2):134-137, ISSN: 1003-1057.

Chen et al., "Lithium Inhibits Ceramide- and Etoposide-induced Protein Phosphatase 2A Methylation, Bcl-2 Dephosphorylation, Caspase-2 Activation, and Apoptosis," 2006, *Molecular Pharmacology*, 70(2):510-517, ISSN: 0026-985X.

Chiang et al., "S-Adenosylmethionine and methylation," 1996, *Faseb J*, 10:471-80.

Cho & Xu, "Crystal Structure of a Protein Phosphatase 2A Heterotrimeric Holoenzyme," 2007, *Nature*, 445:53-57.

Christen et al., "Inhibition of Alpha Interferon Signaling by Hepatitis B Virus," 2007, *J. of Virology*, 81(1):159-165, ISSN: 0022-538X.

Clarke et al., "Folate, Vitamin B$_{12}$, and Serum Total Homocysteine Levels in Confirmed Alzheimer Disease," 1998, *Arch Neurol*, 55:1449-1155.

Clarke et al., "Hyper homocysteinemia: an independent risk factor for vascular disease,", NEJM Apr. 25, 1991, 324(17)1149-1155.

Cohen et al., "Protein Phosphatases Come of Age," 1989, *J. Biol. Chem.*, 264(36):21435-21438.

Cohen et al., "Protein serine/threonine phosphatases; an expanding family," 1990, *FEBS Letters*, 268(2):355-359.

De Baere et al., "Purification of Porcine Brain Protein Phosphatase 2A Leucine Carboxyl Methyltransferase and Cloning of the Human Homologue," 1999, *Biochemistry*, 38(50):16539-16547, ISSN: 0006-2960.

Delgado-Reyes et al., "Immunohistochemical Detection of Betaine-Homocysteine S-Methyltransferase in Human, Pig, and Rat Liver and Kidney," 2001, *Arch Biochem Biophys*, 393(1):184-186.

Deshmukh et al., "Acute Modulation of PP2A and Troponin I Phosphorylation in Ventricular Myocytes: Studies with a Novel PP2A Peptide Inhibitor," 2007, *American Journal of Physiology*, 292(2, Pt. 2):H792-H799, ISSN: 0002-9513.

Deventer et al., "Lower Esophageal Sphincter Pressure, Acid Secretion, and Blood Gastrin after Coffee Consumption," 1992, *Digestive Diseases and Sciences*, 37(4):558-569.

Du, "SmI2 Mediated Aryl Radical Cyclization/Sequential Anionic Capture on Solid Support and Computational Studies on Hapalosin and its Analogs and on Inhibitors of Protein Phosphatases PP1 and PP2A," 1998, University of California, Los Angeles, 58(12):6581.

Dumanchin et al., "Segregation of a missense mutation in the microtubule-associated protein tau gene with familial frontotemporal dementia and parkinsonism," 1998, *Hum. Mol. Genet.*, 7:1825-1829.

Duong et al., "Hepatitis C Virus Inhibits Interferon Signaling through Up-regulation of Protein Phosphatase 2A," 2004, *Gastroenterology*, 126(1):263-277, ISSN: 0016-5085.

Duong et al., "S-adenosylmethionine and Betaine Correct Hepatitis C Virus Induced Inhibition of Interferon Signaling in Vitro," 2006, *Hepatology*, 43(4):796-806, ISSN: 0270-9139.

Duong et al., "Upregulation of Protein Phosphatase 2Ac by Hepatitics C Virus Modulates NS3 Helicase Activity throught Inhibition of Protein Arginine Methyltransferase 1," 2005, *Journal of Virology*, 79(24):15342-15350, ISSN: 0022-538X.

Duval et al., "analogues of cytotoxics squamocin using reliable reactions: new insights into the reativity and role of the α,β-unsaturated lactone of the annonaceous acetogenins," 2006, *Tetrahedron*, 62(26):6248-6257.

Evans et al., "Functional Expression of Human PP2Ac in Yeast Permits the Identification of Novel C-terminal and Dominant-negative Mutant Forms," 1999, *Journal of Biological Chemistry*, 274(34):24038-24046, ISSN: 0021-9258.

Evans et al., "Mutation of the C-terminal Leucine Residue of PP2Ac Inhibits PR55/B Subunit Binding and Confers Supersensitivity to Microtubule Destabilization in *Saccharomyces cerevisiae*," 2000, *Molecular and General Genetics*, 264(4):425-432, ISSN: 0026-8925.

Favre et al., "Differential Inhibition and Posttranslational Modification of Protein Phosphatase 1 and 2A in MCF7 Cells Treated with Calyculin-A, Okadaic Acid, and Tautomycin," 1997, *Journal of Biological Chemistry*, 272(21):13856-13863, ISSN: 0021-9258.

Favre et al., "The Catalytic Subunit of Protein Phosphatase 2A is Carboxyl-Methylated in Vivo," 1994, *Journal of Biological Chemistry*, 269(23):16311-16317, ISSN: 0021-9258.

Finkelstein J.D., "The metabolism of homocysteine: pathways and regultion," 1998, *Eur J Pediatr*, 157(Suppl 2):S40-4.

Floer et al., "Carboxyl Methylation of Protein Phosphatase 2A from *Xenopus* Eggs is Stimulated by cAMP and Inhibited by Okadaic Acid," 1994, *Biochemical and Biophysical Research Communications*, 198(1):372-379, ISSN: 0006-291X.

Folstar et al., "Liquid chromatographic coffee wax analysis," 1977, *Colloque Scientifique International sure le Café*, 8:121-124.

Folstar et al., "Liquid Chromatographie Analysis of N-b)-Alkanoyl-5-Hydroxytryptamine (C-F-HT) in Green Coffee Beans," 1979, *Journal of Agricultural and Food Chemistry*, 27(1):12-15.

Folstar et al., "New tryptamine derivatives isolated from wax of green coffee beans," 1980, *J. Agric. Food Chem.*, 28(4):872-874.

Fowler et al., "Inhibition of Fatty Acid Amidohydrolase, the Enzyme Responsible for the Metabolism of the Endocannabinoid Anandamide, by Analogues of Arachidonoyl-serotonin," 2003, *J. of Enzyme Inhibition and Medicinal Chemistry*, 18(3):225-231.

Fujita, E., "A new efficient aminolysis and its application to synthesis of macrolactam alkaloids," 1981, *Pure and Applied Chemistry*, 53(6):1141-54.

Gentry et al., "A Novel Assay for Protein Phosphatase 2A (PP2A) Complexes In Vivo Reveals Differential Effects of Covalent Modifications on Different *Saccharomyces cerevisiae* PP2A Heterotrimers," 2005, *Eukaryotic Cell*, 4(6):1029-1040, ISSN: 1535-9778.

George et al., "Chaperonin Assisted Overexpression, Purification, and Characterisation of Human PP2A Methyltransferase," 2002, *Protein Expression and Purification*, 26(2):266-274, ISSN: 1046-5928.

Gibbons et al., "Expression of Human Protein Phosphatase-1 in *Saccharomyces cerevisiae* Highlights the Role of Phsphatase Isoforms in Regulating Eukaryotic Functions," 2007, *J. Biol. Chem.*, 282(30):21838-21847.

Goedert et al., "p42 map kinase phophorylation sites in microtubule-associated protein tau are dephosphorylated by protein phosphatase 2A," 1992, *FEBS Letters*, 312(1):95-99.

Goedert et al., "Reduced Binding of protein Phsphatase 2A to Tau Protein with Frontotemporal Dementia and Parkinsonism Linked to Chromosome 17 Mutations," 2000, *J. Neurochem*, 75:2155-2162.

Goldstein et al., "Microtubule-Bases Transport Systems in Nurons: The Roles of Kinesins and Dyneins," 2000, *Annu Rev Neurosci*, 23:39-71.

Gong et al., "Phosphatase activity toward abnormally phosphorylated tau: decrease in Alzheimer disease brain," 1995, J. Neurochem., 65:732-738.

Gonzalez et al., "Total Synthesis of Thyrsiferyl 23-Acetate, a Specific Inhibitor of Protein Phosphatase 2A and an Anti-Leukemic Inducer of Apoptosis," 2000, *Journal of the American Chemical Society*, 122(38):9099-9108, ISSN: 0002-7863.

Gotz, J. et al., "Formation of Neurofibrillary Tangles in P30 1L Tau Transgenic Mice Induced by Aβ42 Fibrils," 2001, Science, 293:1491-1495.

Gozzo et al., "Structure-activity relationships in a series of melatonin analogues with the low-density lipoprotein oxidation model," 1999, *Free Radical Biology & Medicine*, 22(11/12):1538-1543.

Green et al., " Molecular cloning and sequence analysis of the catalytic subunit of bovine type A protein phosphatase," 1987, *Proc Nat'l Acad. Sci USA*, 84:4880-4884.

Greenberg et al., "Hydrofluoric Acid-treated $\tau_{PHF}$ Proteins Display the Same biochemical Properties as Normal $\tau^*$," 1992, *J. Biol. Chem.*, 267(1):564-569.

Guenin et al., "PP2A Activity is Controlled by Methylation and Regulates Oncoprotein Expression in Melanoma Cells: A Mechanism which Participates in Growth Inhibition Induced by Chloroethylnitrosourea Treatment," 2008, International Journal of Oncology, 32(1):49-57, ISSN: 1019-6439.

Guergnon et al., "Use of Penetrating Interacting with PP1/PP2A Proteins as a General Approach for a Drug Phosphatase Technology," 2006, *Mol. Pharmacol.*, 69(4):1115-1124.

Gulledge et al., "Linearized and Truncated Microcystin Analogues as Inhibitors of Protein Phosphatases 1 and 2A," 2003, *Bioorganic & Medicinal Chemistry Letters*, 13(17):2903-2906, ISSN: 0960-840X.

Gulledge et al., "Microcystin Analogues Comprised Only of Adda and a Single Additional Amino Acid Retain Moderate Activity as PP1/PP2A Inhibitors," 2003, *Bioorganic & Medicinal Chemistry Letters*, 13(17):2907-2911, ISSN: 0960-894X.

Guo et al., "ATM-dependent Dissociation of B55 Regulatory Subunit from Nuclear PP2A in Response to Ionizing Radiation," 2002, *Journal of Biological Chemistry*, 277(7):4839-4844, ISSN: 0021-9258.

Hahn et al., "Synthesis of 1-alkylisoquinolines and 1,1'-polymethylenediisoquinolines," 1938, *Berichte der Deutschen Chemischen Gesellschaft [Abteilung] B: Abhandlungen*, 71B:2183-91.

Hahn et al., "Synthesis of 3-alkyl-4-carbolines and 3,3'-polymethylenedi-4-carbolines," 1938, *Berichte der Deutschen Chemischen Gesellschaft [Abteilung] B: Abhandlungen*, 71B:2175-82.

Harms et al., "Carboxylic Acid 5-Hydroxytryptamides in Coffee Beans," 1968, *Zeitschrift fuer Lebensmittel-Untersuchung und-Forschung*, 138(2):75-80. (English language abstract provided as C295).

Hart et al., "Modified Norcantharidins Synthesis, Protein Phosphatases 1 and 2A Inhibition, and Anticancer Activity," 2004, *Bioorganic & Medicinal Chemistry Letters*, 14(8):1969-1973, ISSN: 0960-894X.

Hemmings et al., "α and β Forms of 65-kDA Subunit of Protein Phosphatase 2A Have a Similar 39 Amino Acid Repeating Structure," 1990, *Biochemistry*, 29:3166-3173.

Hendrix et al., "Analysis of Subunit Isoforms in Protein Phosphatase 2A Holoenzymes from Rabbit *Xenopus*," 1993, *J. Biol. Chem.*, 268:7330-7337.

Hill et al., "Heterocyclic Substituted Cantharidin and Norcantharidin Analogues-synthesis, Protein Phosphatase (1 and 2A) Inhibition, and Anti-cancer Activity," 2007, *Bioorganic & Medicinal Chemistry Letters*, 17(12):3392-3397, ISSN: 0960-894X.

Hombauer et al., "Generation of Active Protein Phosphatase 2A is Coupled to Holoenzyme Assembly," 2007, *PLoS Biology*, 5(6):1355-1365, ISSN: 1545-7885.

Hornstein et al., "Protein Phosphatase and TRAIL Receptor Genes as New Candidate Tumor Genes on Chromosome 8p in Prostate Cancer," 2008, *Cancer Genomics & Proteomics*, 5(2):123-136, ISSN: 1109-6535.

Huang et al., "Molecular Cloning, Expression, and Characterization of a Novel Human Serine/Threonine protein Phosphatase, PP7, that is Homologous to *Drosophila* Retinal Degeneration C Gene Product (rdgC)," 1998, *J. Biol. Chem.*, 273(3):1462-1468.

Hubert et al., "Analysis of Carboxylic Acid Hydroxytryptamides in Coffee," 1977, *Fresenius' Zeitschrift fuer Analytische Chemie*, 285(3):242-250.

Hug et al., "Development of a Gas-Liquid Chromatographic Method for the Analysis of Fatty Acid Tryptamides in Cocoa Products," 2006, *J of Agricultural and Food Chemistry*, 54(9):3199-3203.

Hunter et al., "Protein Kinases and Phosphatases: The Ying and Yang of Protein Phosphorylation and Signaling," 1995, *Cell*, 80:225-236.

Hunziker et al., "High-pressure Liquid Chromatographie Determination of 5-Hydroxytryptamide in Coffee," *Mitteilungen aus dem Gebiete der Lebensmitteluntersuchung und Hygiene*, 1979, 70(1), pp. 142-152. (English language abstract provided as C296).

Hunziker, "Determination of 5-Hydroxytryptamide in Coffee Using High-Pressure Liquid Chromatography," 1977, *Mitteilungen aus dem Gebiete der Lebensmitteluntersuchung und Hygiene*, 68(2):267-274. (English language abstract provided as C297).

Hutton et al., "Association of missense and 5'-splice site mutations in tau with the inherited dentia FTDP-17," 1998, *Nature*, 393:702-705.

Ikehara et al., "Baculovirus Expression, Purification, and Characterization of Human Protein Phosphatase 2A Catalytic Subunits α and β," 2006, *Protein Expression and Purification*, 45(1):150-156, ISSN: 1046-5928.

Ikehara et al., "Methylation of the C-terminal Leucine Residue of the PP2A Catalytic Subunit is Unnecessary for the Catalytic Activity and the Binding of Regulatory Subunit (PR55/B)," 2007, *Biochemical and Biophysical Research Communications*, 354(4):1052-1057, ISSN: 0006-291X.

International Search Report for PCT/US2003/07658, Aug. 11, 2003.
International Search Report for PCT/US2006/03686, Jun. 15, 2006.
International Search Report for PCT/US2007/81260, Sep. 11, 2008.
International Search Report for PCT/US2007/82833, Oct. 9, 2008.
International Search Report for PCT/US2009/41321, Jun. 1, 2009.

Jackson-Lewis et al., "Protocol for the MPTP mouse model of Parkinson's disease," 2007, *Nature Protocols*, 2(1):141-152.

Janssen et al., "Fatty Acid Tryptamides as shell indicators for cocoa products and as quality parameters for cocoa butter," 2002, *European Food Research and Technology*, 214(3):259-264.

Janssens et al., "PP2A: the expected tumor suppressor," 2005, *Curr Opin. Genet. Dev.*, 15:34-41.

Janssens et al., "Protein Phosphatase 2A: A Highly Regulated Family of Serine/Threonine Phosphatases Implicated in Cell Growth and Signaling," 2001, *Biochemical Journal*, 353(3):417-439, ISSN: 0264-6021.

Jayaprakasam et al., "Potent lipid peroxidation inhibitors from withania somnifera fruits," 2004, *Tetrahedron* 60(13):3109-3121.

Jiang et al., "The effects of aging on gene expression in the hypothalamus and cortex of mice," 2001, *Proc Natl Acad Sci U S A.* 98(4):1930-1934.

Jicha et al., "Alz-50 and MC-1, a New Monoclonal Antibody Raised to Paired Helical Filaments, Recognize Conformational Epitopes on Recombinant Tau," 1997, *J. Neurosci Res.*, 48(2):128-132.

Kalhor et al., "Protein Phosphatase Methyltransferase 1 (Ppm1p) is the Sole Activity Responsible for Modification of the Major Forms of Protein Phosphatase 2A in Yeast," 2001, *Archives of Biochemistry and Biophysics*, 395(2):239-245, ISSN: 0003-9861.

Kamibayashi et al., "Comparison of Heterotrimeric protein Phosphatase 2A Containing Different B Subunits," 1994, *J. Biol. Chem.*, 269(31):20139-20148.

Keen et al., "Epigenetic Regulation of Protein Phosphatase 2A (PP2A), Lymphotactin (XCL1) and Estrogen Receptor Alpha (ER) Expression in Human Breast Cancer Cells," 2004, *Cancer Biology & Therapy*, 3(12):1304-1312, ISSN: 1538-4047.

Kele et al., Determination of serotonin released from coffee wax by liquid chromatography, 1996, *J. of Chromatography*, 730:59-62.

Khew-Goodall et al., "Tissue-specific expression of mRNAs encoding α and β catalytic subunits of protein phosphatase 2A," 1988, *FEBS Lett*, 238:265-268.

Khil et al., "Hydrogen Peroxide Mediates Brazilin-induced Glucose Transport in Adipocytes," 2004, *Journal of Applied Pharmacology*, 12(4):228-234, ISSN: 1225-6110.

Kins et al., "Reduced Poteing Phosphatase 2A Activity Induces Hyperphosphorylation and Altered Compartmentalization of Tau in Transgenic Mice," 2001, *J Biol Chem*, 276:38193-200.

Kita et al., "Structure-activity Relationship of Okadaic Acid, a Potent Protein Phosphatases PP1 and PP2A Inhibitor: 24-Epi-Okadaic Acid and a 18-membered Lactone Analog," 2008, *Heterocycles*, 76(2), pp. 1033-1042, ISSN: 0385-5414.

Kloeker et al., "Carboxymethylation of Nuclear Protein Serine/Threonine Phosphatase X," 1997, *Biochemical Journal*, 327(2):481-486, ISSN: 0264-6021.

Kobayashi et al., "Process Formation of Podocytes: Morphogenetic Activity of Microtubules and Regulation by Protein Serine/Threonine Phosphatase PP2A," 2001, *Histochemistry and Cell Biology*, 115(3):255-266, ISSN: 0948-6143.

Koenig et al., "Gas Chromatography and Mass Spectrometry as Aids in Studying High-Boiling Coffee Compounds," Institut fur Organische Chemie and Biochemie, pp. 271-278; and Colloque Scientifique International sur le Cafe (1983), Volume Date 1982, 10th. (English language abstract provided as C297).

Konoki et al., "Direct Observation of Binding Between Biotinylated Okadaic Acids and Protein Phosphatase 2A Monitored by Surface Plasmon Resonance," 1999, *Tetrahedron Letters*, 40(5):887-890, ISSN: 0040-4039.

Koren et al., "The Scaffolding A/Tpd3 Subunit and High Phosphatase Activity are Dispensable for Cdc55 Function in the *Saccharomyces cerevisiae* Spindle Checkpoint and in Cytokinesis," 2004, *Journal of Biological Chemistry*, 279(47), 48598-48606, ISSN: 0021-9258.

Kowluru et al., "Carboxylmethylation of the Catalytic Subunit of Protein Phosphatase 2A in Insulin-secreting Cells: Evidence for Functional Consequences on Enzyme Activity and Insulin Secretion," 1996, *Endocrinology*, 137(6):2315-2323, ISSN: 0013-7227.

Kowluru et al., "Ceramide-activated Protein Phosphatase-2A Activity in Insulin-secreting Cells," 1997, *FEBS Letters*, 418(1,2):179-182, ISSN: 0014-5793.

Kowluru et al., "Purine Nucleotide- and Sugar Phosphate-induced Inhibition of the Carboxyl Methylation and Catalysis of Protein Phosphatase-2A in Insulin-secreting Cells: Protection by Divalent Cations," 1998, *Bioscience Reports*, 18(4):171-186, ISSN: 0144-8463.

Kowluru, "Bridging the Gap Between Protein Carboxyl Methylation and Phospholipid Methylation to Understand Glucose-stimulated Insulin Secretion from the Pancreatic β Cell," 2008, *Biochemical Pharmacology*, 75(2):335-345, ISSN: 0006-2952.

Kraulis, "MOLSCRIPT: a program to produce both detailed and schematic plots of protein structures," 1991, *J. Appl. Crystallogr.*, 24:946-950.

Krebs & Fisher, "Conversion of Phosphorylase β to Phosphorylase α in Muscle Extracts," 1955, *J. Biol. Chem.*, 216:121-132.

Krebs & Fisher, "Phosphorylase Activity of Skeletal Muscle Extracts," 1955, *J. Biol. Chem.*, 216:113-120.

Kurzrock et al., "Chromatography of Carbonic Acid-5-Hydroxyltryptamides," *Institute of Food Chemistry*, pp. 305-308; and *Colloque Scientifique International sur le Cafe* (2005), Date 2004, 20th.

Lang et al., "A Versatile Method for the Quantitative Determination of bN-Alkanoyl-5-Hydroxytryptamides in Roasted Coffee," 2005, *European Food Research and Technology*, 220(5-6):638-643.

Laub et al., "[ADMAdda5]-microcysins in *Planktothrix agardhii* Strain PH-123 (Cyanobacteria)—Importance of Monitoring of Microcystins in the Environment," 2002, *Environmental Toxicology*, 17(4):351-357, ISSN: 1520-4081.

Lawhorn et al., "Total Synthesis and Evaluation of Cytostatin, Its C10-C11 Diastereomers, and Additional Key Analogues: Impact on PP2A Inhibition," 2006, *Journal of the American Chemical Society*, 128(51):16720-16732, ISSN: 0002-7863.

Lawhorn et al., "Total Synthesis of Cytostatin," 2006, *Heterocycles*, 70:65-70, ISSN: 0385-5414.

Le Bars et al., "Influence of the Severity of Cognitive Impairment on the Effect of the *Ginkgo* biloba Extract EGb 761 in alzheimer's Disease," 2002, *Neuropsychobiology*, 45:19-26.

Lechward et al., "Protein Phosphatase 2A: Variety of Forms and Diversity of Functions," 2001, *Acta Biochimica Polonica*, 48(4):921-933, ISSN: 0001-527X.

Lee et al., "A Specific Protein Carboxyl Methylesterase that Demethylates Phosphoprotein Phosphatase 2A in Bovine Brain," 1996, *Proceedings of the National Academy of Sciences of the United States of America*, 93(12):6043-6047, ISSN: 0027-8424.

Lee et al., "Leucine Carboxyl Methyltransferase-1 is Necessary for Normal Progression through Mitosis in Mammalian Cells," 2007, *Journal of Biological Chemistry*, 282(42):30974-30984, ISSN: 0021-9258.

Lee et al., "Mechanisms of Parkinson's Deseas Linked to Pathological α Synuclein: New Targets for Drug Discovery," 2006, *Neuron*, 52:33-38.

Lee et al., "Neurodegenerative Tauopathies," 2001, *Annu Rev Neurosci*, 24:1121-1159.

Lee et al., "Protein Phosphatase 2A Catalytic Subunit Is Methylesterified at Its Carboxyl Terminus by a Novel Methyltransferase," 1993, *J. Biol. Chem.*, 268(26):19192-19195.

Leulliot et al., "Structure of Protein Phosphatase Methyltransferase 1 (PPM1), a Leucine Carboxyl Methyltransferase Involved in the Regulation of Protein Phosphatase 2A Activity," 2004, *Journal of Biological Chemistry*, 279(9):8351-8358, ISSN: 0021-9258.

Lewis et al., "Enhanced Neurofibrillary Degeneration in Transgenic Mice Expressing Mutant Tau and APP," 2001, *Science*, 293:1487-1491.

Li et al., "Disruption of microtubule network by Alzheimer abnormally hyperphosphorylated tau," 2007, *Acta Neuropathol.*, 113:501-11.

Li et al., "Okadaic Acid and Microcystin-LR Directly Inhibit the Methylation of Protein Phosphatase 2A by its Specific Methyltransferase," 1994, *Biochemical and Biophysical Research Communcations*, 202(2):1023-1030, ISSN: 0006-291X.

Li, Zhu, "Post-Translational Carboxyl Methylation of Protein Phosphatase 2A: a Therapeutic Target," 2008, *Dissertation Presented to Dept. of Chemistry at Princeton University*, 1-175.

Lim et al., "The Curry Spice Curcumin Redues Oxidative Damage and Amyloid Pathology in an Alzheimer Transgenic Mouse," 2001, *J of Neuroscience*, 21(2):8370-8377.

Lindsay et al., "Risk Factors for Alzheimer's Disease: A Prospective Analysis from the Canadian Study of Health and Aging," 2002, *Am. J. Epidemiol.*, 156(5):445-53.

Litvan, Irene, "Update on Epidemiological Aspects of Progressive Supranulear Palsy," 2003, *Movement Disorders*, 18(6):S43-S50.

Liu et al., "Antiadrenergic Effects of Adenosine A1 Receptor-mediated Protein Phosphatase 2a Activation in the Heart," 2002, *American Journal of Physiology, Heart and Circulatory Physiology*, 283(4, Pt. 2):H1314-H1321, ISSN: 0002-9513.

Longin et al., "Selection of Protein Phosphatase 2A Regulatory Subunits is Mediated by the C Terminus of the Catalytic Subunit," 2007, *Journal of Biological Chemistry*, 282(37):26971-26980, ISSN: 0021-9258.

Lucock, M., "Folic Acid: Nutritional biochemistry, Molecular Biology, and Role in Disease Processes," 2000, *Mol Genet Metab*, 71:121-138.

Maeda et al., "N-Fatty acyl tryptamines from Annona reticulata," 1993, *Phytochemistry*, 34(6):1633-5.

Maki et al., "Catalyst-controlled Asymmetric Synthesis of Fostriecin and 8-epi-Fostriecin," 2005, *Journal of the American Chemical Society*, 127(48):17111-17117, ISSN: 0002-7863.

Mancini et al., "Synthesis and Bioactivity of Linear Oligomers Related to Polymeric Alkylpyridinium Metabolites from the Mediterranean Sponge *Reniera sarai*," 2004, *Organic & Biomolecular Chemistry*, 2(9):1368-1375, ISSN: 1477-0520.

Manning et al., "The Protein Kinase Complement of the Human Genome," 2002, *Science*, 298:1912-1934.

Mano, M.L., "Silicic acid column chromatography in the separation of components of food fats," 1965, *Revista Portuguesa de Farmacia*, 15(3):398-401.

Martin De La Vega et al., "Cerebral Postischemic Reperfusion-induced Demethylation of the Protein Phosphatase 2A Catalytic Subunit," 2002, *Journal of Neuroscience Research*, 69(4):540-549, ISSN: 0360-4012.

Martin et al., "Identification and determination of peanut oil mixed with permissible edible oils," 1964, *Medicamenta*, 32(16):9-12.

Marx, J., "Alzheimer disease: A new take on tau," 2007, *Science*, 316(5830):1416-1417.

Maude et al., "Design and Preparation of Serine-Threonine Protein Phosphatase Inhibitors Based Upon the Nodularin and Microcystin Toxin Structures: Part 2. Synthesis of a Functionalized Nodularin Macrocycle and a Stripped-down Microcystin Macrocycle," 1997, *Journal of the Chemical Society, Perkin Transactions 1: Organic and Bio-Organic Chemistry*, 17:2513-2526, ISSN: 0300-922X.

Mazanetz et al., "Untangling tau hyperphosphorylation in drug design for neurodegenerative disease," 2007, *Nat. Rev. Drug Discovery*, 6:464-479.

McCaddon et al., "Total Serum Homocysteine in Senile Dementia of Alzheimer Type," 1998, *Int J Geriatr Psychiatry*, 13:235-239.

McCluskey et al., "Anhydride Modified Cantharidin Analogues. Is Ring Opening Important in the Inhibition of Protein Phosphatase 2A," 2000, *European Journal of Medicinal Chemistry*, 35(10):957-964, ISSN: 0223-5234.

McCluskey et al., "Anhydride Modified Cantharidin Analogues: Synthesis, Inhibition of Protein Phosphatases 1 and 2A and Anticancer Activity," 2000, *Bioorganic & Medicinal Chemistry Letters*, 10(15):1687-1690, ISSN: 0960-0894X.

McCluskey et al., "The First Two Cantharidin Analogues Displaying PP1 Selectivity," 2002, *Bioorganic & Medicinal Chemistry Letters*, 12(3):391-393, ISSN: 0960-894X.

McCluskey et al., "The Inhibition of Protein Phosphatases 1 and 2A: A New Target for Rational Anti-Cancer Drug Design," 2001, *Anti-Cancer Drug Design*, 16:291-303.

Mehrotra et al., "Design and Preparation of Serine-Threonine Protein Phosphatase-inhibitors Based Upon the Nodularin and Microcystin Toxin Structures. Part 1. Evaluation of Key Inhibitory Features and Synthesis of a Rationally Stripped-down Nodularin Macrocycle," 1997, *Journal of the Chemical Society, Perkin Transactions 1: Organic and Bio-Organic Chemistry*, 17:2495-2511, ISSN: 0300-922X.

Merrick et al., "Selective Destruction of Stable Mictotubules and Axons by Inhibitors of Protein Serine/Threonine Phosphatases in Cultured Human Neurons (NT2N Cells)," 1997, *J Neurosci*, 17:5726-5737.

Miyashita et al., "Synthetic Studies on Fostriecin and Related Natural Products," 2007, *Yuki Gosei Kagaku Kyokaishi*, 65(9):874-887, ISSN: 0037-9980. (English language abstract included on first page of document).

Moller et al., "Okadaic Acid-induced, Naringin-sensitive Phosphorylation of Glycine N-methyltransferase in Isolated Rat Hepatocytes," 2003, *Biochemical Journal*, 373(2):505-513, ISSN: 0264-6021.

Moreno et al., "Down-Regulation of the Homeodomain Factor Cdx2 in Colorectal Cancer by Collagen Type I: An Active Role for the Tumor Environment in Malignant Tumor Progression," 2004, *Cancer Res.*, 64:6978-6988.

Mumby M., "The 3D Structure of Protein Phosphatase 2A: New Insights into a Ubiquitous Regulator of Cell Signaling," 2007, *ACS Chemical Biology*, 2(2):99-103, ISSN: 1554-8929.

Munch et al., "A sensitive and seletive method for the quantitative determination of fatty acid tryptamides as shell indicators in cocoa products," 1999, *Zeitschrift fuer Lebensmittel-Untersuchung und-Forschung A: Food Research and Technology*, 208(1):39-43.

Munch et al., "Characterization of the substances in cocoa shell. Possibilities to determine the shell percentage in cocoa products by indicators," 1999, *Lebensmittelchemie*, 53(6):148.

Nagao et al., "Monitored aminolysis of 3-acylthiazolidine-2-thione: a new convenient synthesis of amide," 1980, *Tetrahedron Letters*, 21(9):841-4.

Nagao et al., "Studies on a new synthesis of the acyclic amide and macrocyclic lactam alkaloids," 1979, *Koen Yoshishu-Tennen Yuki Kagobutsu Torankai*, 22nd, 554-61.

Nagao et al., "Utilization of sulfur-containing leavng groups. Part IV. Monitored aminolysis of 3-acyl-1,3-thiazolidine-2-thiones: synthesis of amides and amide alkaloids," 1984, *Chemical & Pharmaceutical Bulletin*, 32(7):2687-99.

Nebesny et al., "Effect of the Roasting Method on the Content of 5-Hydroxytryptamides of Carboxylic Acids in Roasted Coffee Beans," 2002, *Nahrung*, 46(4):279-282.

Netland, et al., "Indomethacin Reverses the Microglial Response to Amyloid β-Protein," 1998, *Neurobiology of Aging*, 19(3):201-204.

Neviani et al., "FTY720, a new alternative for treating blast crisis chronic myelogenous leukemia and Philadelphia chromosome-positive acute lymphocytic leukemia," 2007, *J of Clinical Investigation*, 17(9):2408-2421.

Nicholls et al., "Protein Folding and Association: Insights from the Interfacial and Thermodynamic Properties of Hydrocarbons," 1991, *Proteins: Struct. Funct. Genet.*, 11:281-296.

Nien et al., "Overexpression of the mTOR Alpha4 Phosphoprotein Activates Protein Phosphatase 2A and Increases Stat1α Binding to PIAS1," 2007, *Molecular and Cellular Endocrinology*, 263(1-2):10-17, ISSN: 0303-7207.

Nishiyama, et al., "Ameliorative Effect of S-Allylcysteine, a Major Thioallyl Constituent in Aged Garlic Extract, on learning Deficits in Senescence-Accelerated Mice," 2001, *American Society for Nutritional Sciences*, 1093S-1095S.

Nowotny et al., "Association studies between common variants in prolyl isomerase *Pin1* and the risk for late-onset Alzheimer's disease," 2007, Neuroscience Letters, 419(1):15-7.

Nunbhakdi-Craig et al., "Expression of Protein Phosphatase 2A Mutants and Silencing of the Regulatory Bβ Subunit Induce a Selective Loss of Acetylated and Detyrosinated Microtubules," 2007, *Journal of Neurochemistry*, 101(4):959-971, ISSN: 0022-3042.

Ogawa et al., "Asymmetric Synthesis of Calyculin C. 2. Synthesis of the C26-C37 Fragment and Model Wittig Couplings," 1996, *Journal of Organic Chemistry*, 61(18):6153-6161, ISSN: 0022-3263.

Ogawa et al., "Total Synthesis of Calyculin C," 1998, *Journal of the American Chemical Society*, 120(48):12435-12442, ISSN: 0002-7863.

Ogris et al., "A Protein Phosphatase Methylesterase (PME-1) is One of Several Novel Proteins Stably Associating with Two Inactive Mutants of Protein Phosphatase 2A," 1999, *Journal of Biological Chemistry*, 274(20):14382-14391, ISSN: 0021-9258.

Oikawa et al., "Synthetic Study of Tautomycetin and Biological Activity of Tautomycin Derivatives," 1997, *Tennen Yuki Kagobutsu Toronkai Koen Yoshishu*, 39:433-438. (English language abstract included on first page of document).

Oikawa, "Synthesis of Specific Protein Phosphatase Inhibitors, Tautomycin and Tautomycetin Toward Structure-activity Relationship Study," 2002, *Current Medicinal Chemistry*, 9(22):2033-2054, ISSN: 0929-8673.

Ortega-Gutierrez et al., "Targeted Disruption of the PME-1 Gene Causes Loss of Demethylated PP2A and Perinatal Lethality in Mice," 2008, *PLoS One*, 3(7)e2486:1-9, ISSN: 1932-6203.

Otvos et al., "Monoclonal Antibody PHF-1 Recognizes Tau Protein Phosphorylated at Serine Residues 396 and 404," 1994, *J. Neurosci Res.*, 39(6):669-673.

Paterson et al., "Total Synthesis of Spirastrellolide A Methyl Ester-part 1: Synthesis of an Advanced C17-C40 Bis-spiroacetal Subunit," 2008, *Angewandte Chemie, International Edition*, 47(16):3016-3020, ISSN: 1433-7851.

Peng et al., "Induction of Apoptosis by Norcantharidin in Human Colorectal Carcinoma Cell Lines: Involvement of the CD95 Receptor/Ligand," 2002, *Journal of Cancer Research and Clinical Oncology*, 128(4):223-230, ISSN: 0171-5216.

Pihko et al., "Synthesis of the C26-C32 Oxazole Fragment of Calyculin C: A Test Case for Oxazole Syntheses," 1998, *Journal of Organic Chemistry*, 63(1):92-98, ISSN: 0022-3263.

Planel et al., "Inhibition of Protein Phosphatase 2A Overrides Tau Protein Kinase I/Glycogen Synthase Kinase 3β and Cyclin-dependent Kinase 5 Inhibition and Results in Tau Hyperphosphorylation in the Hippocampus of Starved mouse," 2001, *J. Biol. Chem.*, 276(36):34298-34306.

Potter, et al., "The inflammation-induced pathological chaperones ACT and apo-E are necessary catalysts of Alzheimer amyloid formation," 2001, *Neurobiology of Aging*, 22:923-930.

Rajagopalan et al., "Molecular Biology of C4 Phosphoenolpyruvate Carboxylase: Structure, Regulation and Genetic Engineering," 1994, *Photosynthesis Research*, 39(2):115-135, ISSN: 0166-8595.

Rametti et al., "Linking Alterations in Tau Phosphorylation and Cleavage during Neuronal Apoptosis," 2004, *J. Biol. Chem.*, 279:54518-54528.

Refsum et al., "Homocystein and Cardiovascular Disease," 1998, *Annu. Rev. Medicine*, 49:31-62.

Rizzu et al., "High prevalence of mutations in the microtubule-associated protein tau in a population of study of frontotemporal dementia in the Netherlands," 1999, *Am. J. Hum. Genet.*, 64:414-421.

Roder et al., "Microtubule-associated protein tau as a therapeutic target in neurodegenerative disease," 2007, *Expert Opinion ther. Targets*, 11(4):435-442.

Roszkowski et al., "Enantioselective synthesis of 1-substituted tetrahydro-β-carboline derivatives via asymmetric transfer hydrogenation," 2005, *J. of Molecular Catalysis A: Chemical*, 232(1-2):143-149.

Rusnak et al., "Calcineurin: Form and Function," 2000, *Physiological Reviews*, 80(4):1483-1521.

Sacher et al., "Behenic acid tryptamide, a component of cocoa shell," 1965, *Zeitschrift fuer Lebensmittel-Untersuchung und-Forschung* 128(5):264-7.

Sakoff & McCluskey, "Protein Phosphatase Inhibition: Structure Based Design. Towards new Therapeutic Agents," 2004, *Current Pharmaceutical Design*, 10:1139-1159.

Sakoff et al., "Anticancer Activity and Protein Phosphatase 1 and 2A Inhibition of a New Generation of Cantharidin Analogues," 2002, *Investigational New Drugs*, 20(1):1-11, ISSN: 0167-6997.

Salit et al., "Synthetic Studies Toward Cytostatin, a Natural Product Inhibitor of Protein Phosphatase 2A," 2008, *Tetrahedron*, 64(28):6684-6697, ISSN: 0040-4020.

Scarlato et al., "Asymmetric Synthesis of Calyculin C. 1. Synthesis of the C1-C25 Fragment," 1996, *Journal of Organic Chemistry*, 61(18):6139-6152, ISSN: 0022-3263.

Schnyder et al., " Decreased Rate of Coronary Restenosis After Lowering of Plasma Homocysteine Levels," 2001, *N Engl J Med*, 345:1593-1600.

Schwartz et al., "Hyperosmotic Stress Contributes to Mouse Colonic Inflammation through the Methylation of Protein Phosphatase 2A," 2008, *American Journal of Physiology*, 295(5, Pt. 1):G934-G941, ISSN: 0002-9513.

Sciortino et al., "Antiviral activity. IX. Higher acyl derivatives of sympathomimetic amines of biological significance," 1968, *Bollettino Chimico Farmaceutico*, 107(8):506-11.

Scott and Weir, "Folic acid, homocysteine and one-carbon metabolism: a review of the essential biochemistry," 1998, *J Cardiovasc Risk*, 5:223-227.

Scott B., "Protein Phosphatase 2A methylation," 2002, *FEBS Letters*, 518(1-3):1-4.

Selhub et al., "B vitamins, homocysteine, and neurocognitive function in the elderly," 2000, *Am J Clin Nutr*, 71:614S-620S.

Selhub et al., "Vitamin Status and Intake as Primary Determinants of Homocysteinemia in an Elderly Population," 1993, *JAMA*, 270:2693-2698.

Selhub, "Homocysteine Metabolism," 1999, *Annu Rev Nutr*, 19:217-246.

Selhub, et al., "Serum Total Homocysteine Concentrations in the Third National Health and Nutrition Examination Survey (1991-1994): Population Reference Ranges and Contribution of Vitamin Status to High Serum Concentrations," 1999, *Ann. Intern. Med.*, 131(5):331-339.

Selkoe, "Alzheimer's Disease: Genes, Proteins, and Therapy," 2001, *Physiol Rev.* 81:741-66.

Seshadri et al., "Plasma Homocystein as a Risk Factor for Dementia and Alzheimer's Disease," 2002, *New England J. of Med.*, 346(7):476.

Sherpina et al., "Ginkgo Biloba," 2003, *American Family Physician*, 68(5):923-926.

Shibasaki et al., "Synthetic Strategies of Fostriecin," 2005, *Heterocycles*, 66(1):727-741, ISSN: 0385-5414.

Somei et al., "The chemistry of indoles. 87. Syntheses of 1-hydroxytryptamines and serotonins having fatty acyl or (E)-3-phenylpropenoyl derivatives as a Nb-substituent, and a novel homologation on the 3-substituent of the 1-hydroxytryptamines upon treatment with diazomethane," 1998, *Heterocycles* 48(6):1117-1120.

Sontag et al., "A Novel Pool of Protein Phosphatase 2A Is Associated with Microtubules and Is Regulated during the Cell Cycle," 1995, *J Cell Biol*, 128:1131-1144.

Sontag et al., "Altered Expression Levels of the protein Phosphatase 2A ABαC Enzyme are Associated with Alzheimer Disease Pathology," 2004, *Journal of Neuropathology and Experimental Neurology*, 63(4):287-301.

Sontag et al., "Downregulation of Protein Phosphatase 2A Carboxyl Methylation and Methyltransferase May Contribute to Alzheimer Disease Pathogenesis," 2004, *Journal of Neuropathology and Experimental Neurology*, 63(10):1080-1091, ISSN: 0022-3069.

Sontag et al., "Molecular Interactions among Protein Phosphatase 2A, Tau, and Microtubules," 1999, *J. Biol. Chem.*, 274(36):25490-25498.

Sontag et al., "Protein Phosphatase 2A Methyltransferase Links Homocysteine Metabolism with Tau and Amyloid Precursor Protein Reguatlion," 2007, *Journal of Neuroscience*, 27(11):2751-2759, ISSN: 0270-6474.

Sontag et al., "Regulation of Phosphorylation State and Microtubule-Binding Activity of tau by Protein Phosphatase 2A," 1996, *Neuron*, 17:1201-1207.

Sontag, E. "Protein phosphatatase 2A: the Trojan Horse of Cellular signaling," 2001, *Cell. Signaling*, 13:7-16.

Stock et al., "A protein methylesterase involved in bacterial sensing," 1978, *Proc. Natl. Acad. Sci. USA*, 75(8):3659-3663.

Stone et al., "Molecular Cloning of cDNAs Encoding Two Isoforms of the Catalytic Subunit of Protein Phosphatase 2A," 1987, *Biochemistry*, 26:7215-7220.

Studer et al., "Quantitative HPTLC Determination of Carbon-5-Hydroxytryptamides and Tryptamines in Food Products," 1982, *Journal of High Resolution Chromatography & Chromatography Communications*, 5(10358):581-582.

Sun et al., "Inhibition of Protein Phosphatase 2A- and Protein Phosphatase 1-Induced Tau Hyperphosphorylation and Impairment of Spatial Memory Retention in Rats," 2003, *Neuroscience*, 118:1175-1182.

Sunahori et al., "Methylation Status of CpG Islands Flanking a cAMP Response Element Motif on the Protein Phosphatase 2Acα Promoter Determines CREB Binding and Activity," 2009, *Journal of Immunology*, 182(3):1500-1508, ISSN: 0022-1767.

Swiatek et al., "Biochemical Characterization of Recombinant Subunits of Type 2A Protein Phosphatase Overexpressed in *Pichia pastoris*," 2000, *European Journal of Biochemistry*, 267(16):5209-5216, ISSN: 0014-2956.

Szelag et al., "Determination of the amount of hull-derived lipids in cocoa oils," 1984, *Przemysl Spozywczy* 38(9):355-7.

Szelag et al., "Evaluation of behenic acid tryptamide in cocoa fat on the basis of blue value dterminations," 1988, *Nahrung*, 32(3):285-90.

Taylor et al., "Potent Non-peptidyl Inhibitors of Protein Tyrosine Phosphatase 1 B," 1998, *Bioorganic & Medicinal Chemistry*, 6(9):1457-1468, IISSN: 0968-0896.

Taylor et al., "Potent Non-peptidyl Inhibitors of Protein Tyrosine Phosphatase 1 B. [Erratum to document cited in CA130:3892]," 1998, *Bioorganic & Medicinal Chemistry*, 6(11):2235, ISSN: 0968-0896.

Tolstykh et al., "Carboxyl Methylation Regulates Phosphoprotein Phosphatase 2A by Controlling the Association of Regulatory B Subunits," 2000, *EMBO Journal*, 19(21):5682-5691, ISSN: 0261-4189.

Travesa et al., "Distinct Phosphatases Mediate the Deactivation of the DNA Damage Checkpoint Kinase Rad53," 2008, *Journal of Biological Chemistry*, 283(25):17123-17130, ISSN: 0021-9258.

Tsujio et al., "Inhibitors of protein phosphatase-2A from human brain structures, immunocytological localization and activities towards dephosphorylation of the Alzheimer type hyperphosphorylated tau," 2005, *FEBS Lett*, 579:363-372.

Turowski et al., "Differential Methylation and Altered Conformation of Cytoplasmic and Nuclear Forms of Protein Phosphatase 2A During Cell Cycle Progression," 1995, *Journal of Cell Biology*, 129(2):397-410, ISSN: 0021-9525.

Tverdal et al., "Coffee Intake and Mortality from Liver Cirrhosis," 2003, *AEP* 13(6):419-423.

Tyas, S., "Are tobacco and alcohol use related to Alzheimer's disease? A critical assessment of the Evidence and its Implications" 1996, *Addiction Biology*, 1(3):237.

Vafai et al., "Protein phosphatase 2A methylation: a link between elevated plasma homocysteine and Alzheimer's Disease," 2002, *FEBS Letters*, 518:1-4.

Van Dam et al., "Coffee consumption and risk of type 2 diabetes mellitus," 2002, *The Lancet*, 360:1477.

Virshup, D., "Protein phosphatase 2A: a panoply of enzymes," 2000, *Curr Opin. Cell Biol.*, 12:180-185.

Vogelsberg-Ragaglia et al., "PP2A mRNA Expression Is Quantitatively Decreased in Alzheimer's Disease Hippocampus," 2001, *Exp Neurol*, 168:402-412.

Wang et al., "Inhibition of Growth and p21$^{ras}$ Methylation in Vascular Endothelial Cells by Homocysteine but Not Cysteine," 1997, *J Biol Chem*, 272:25380-25385.

Webster et al., "Design and Preparation of Serine-Threonine Protein Phosphatase Inhibitors Based Upon the Nodularin and Microcystin Toxin Structures. Part 3," 2001, *Journal of the Chemical Society, Perkin Transactions 1*, 14:1673-1695, ISSN: 1472-7781.

Wei et al., "Carboxymethylation of the PP2A Catalytic Subunit in *Saccharomyces cerevisia* is Required for Efficient Interaction with the B-type Subunits Cdc55p and Rts1p," 2001, *Journal of Biological Chemistry*, 276(2):1570-1577, ISSN: 0021-9258.

Welch, G.N. and Loscalzo, J., "Homocysteine and Atherothrombosis," 1998, *N Engl J Med*, 338:1042-1050.

Wera et al., "Serine/threonine protein phosphatases," 1995, *Biochem. J.*, 311:17-19.

Wiart et al., "Sesquiterpenes and Alkaloids from Scorodocarpus Borneensis," 2001, *Phytochemistry*, 58(4):653-656.

Williams et al., "Spirastrellolide A: A Revised Structure, Progress Toward the Relative Configuration, and Inhibition of Protein Phosphatase 2A," 2004, *Organic Letters*, 6(15):2607-2610, ISSN: 1523-7060.

Written Opinion for PCT/US2007/81260, Sep. 11, 2008.

Written Opinion for PCT/US2007/82833, Oct. 9, 2008.

Wu et al., "Carboxyl Methylation of the Phosphoprotein Phosphatase 2A Catalytic Subunit Promotes its Functional Association with Regulatory Subunits in vivo," 2000, *EMBO J*, 19(21):5672-5681.

Wu et al., "Tryptamine-Derived Amides and Alkaloids from the Seeds of Annona atemoya," 2005, *J. of Natural Products*, 68(3):406-408.

Wurziger et al., "Hydroxytrypatamides of Green and Roasted Coffee Beans," 1969, *Presented at Association Scientifique Internationale du Cafe, 4th International Colloquium on the Chemistry of Coffee*, 85-91.

Wurziger et al., "Chemistry of Cocoa. Carboxylic Acid-5-Hydroxytryptamide in Cocoa Beans," 1970, *Hyg. Inst., Gordian*, 70(1644), Part 2:438-440. (English language abstract included on first page of reference C276).

Wurziger et al., "Chemistry of Cocoa. Carboxylic Acid-5-Hydroxytryptamide in Cocoa Beans," 1970, *Hyg. Inst., Gordian*, 70(1645), Part 3:470-473. (English language abstract included on first page of reference C276).

Wurziger et al., "Chemistry of Cocoa. Carboxylic Acid-5-Hydroxytryptamide in Cocoa Beans," 1970, *Hyg. Inst., Gordian*, 70(1643), Part 1:376-378. (English language abstract included on first page of document).

Xie et al., "An Enzymic Activity in Bovine Brain that Catalyzes the Reversal of the C-terminal Methyl Esterification of Protein Phosphatase 2A," 1994, *Biochemical and Biophysical Research Communications*, 203(3):1710-1715, ISSN: 0006-291X.

Xie et al., "Protein Phosphatase 2A is Reversibly Modified by Methyl Esterification at its C-terminal Leucine Residue in Bovine Brain," 1994, *Journal of Biological Chemistry*, 269(3):1981-1984, ISSN: 0021-9258.

Xing et al., "Structural Mechanism of Demethylation and Inactivation of Protein Phosphatase 2A," 2008, *Cell*, 133(1):154-163, ISSN: 0092-8674.

Xing et al., "Structure of protein phosphatase 2A core enzyme bound to tumor-inducing toxins," 2006, *Cell*, 127(2):341-353.

Xoe et al., "Methyl Esterification of C-terminal Leucine Residues in Cytosolic 36-kDa Polypeptides of Bovine Brain," 1993, *J. of Biological Chemistry*, 268(18):13364-13371.

Xu et al., "Structure of the Protein Phosphatase 2A Holoenzyme," 2006, *Cell*, 127(6):1239-1251.

Yang et al., "S-adenosylemthionine and its Metabolite Induce Apoptosis in HepG2 Cells: Role of Protein Phosphatase 1 and Bcl-xS," 2004, *Hepatology*, 40(1):221-231, ISSN: 0270-9139.

Yi et al., "Increase in Plasma Homocysteine Associated with Parallel Increase in Plasma S-Adenosylhomocysteine and Lymphocyte DNA Hypomethylation," 2000, *J Biol Chem*, 275:29318-29323.

Yoo et al., "The α4-containing Form of Protein Phosphatase 2A in Liver and Hepatic Cells," 2008, *Journal of Cellular Biochemistry*, 105(1):290-300, ISSN: 0730-2312.

Yoon et al., "Methotrexate Decreases PP2A Methylation and Increases Tau Phosphorylation in Neuron," 2007, *Biochemical and Biophysical Research Communications*, 363(3):811-816, ISSN: 0006-291X.

Yu et al., "Methylation of the Protein Phosphatase 2A Catalytic Subunit is Essential for Association of Bα Regulatory Subunit but not SG2NA, Striatin, or Polyomavirus Middle Tumor Antigen," 2001, *Molecular Biology of the Cell*, 12(1):185-199, ISSN: 1059-1524.

Zhang et al., "Homocysteine Induces Tau Phosphorylation by Inactivating Protein Phosphatase 2A in Rat Hippocampus," 2008, *Neurobiology of Aging*, 29(11):1654-1665, ISSN: 0197-4580.

European Search Opinion, Communication regarding the transmission of the European Search Report, and Supplementary European Search Report for EP 1843734, Aug. 7, 2008.

O'Donnell et al., "Serine-threonine protein phosphatase inhibitors derived from nodularin: role of the 2-methyl and 3-diene groups in the Adda residue and the effect of macrocyclic conformational restraint," 2001, *J. Chem. Soc., Perkin Trans.*, 1:1696-1708.

Ryu et al., 2006, "Photo- and electroluminescent properties of cyano-substituted styryl derivatives and synthesis of CN-PPV model compounds containing an alkoxy spacer for OLEDs," *Tetrahedron*, 62:6236-47.

Written Opinion for PCT/US2006/003686, Aug. 2, 2007.

Xie and Clarke, 1993, "Methyl esterification of C-terminal leucine residues in cytosolic 36-kDa polypeptides of bovine brain," *J. Biol. Chem.*, 268(18):13364-71.

Zhou et al., 2008, "Tau hyperphosphorylation correlates with reduced methylation of protein phosphatase 2A," *Neurobiology of Disease*, 31:386-94.

English language abstract of C89 (Harms et al., "Carboxylic Acid 5-Hydroxytryptamides in Coffee Beans," 1968, *Zeitschrift fuer Lebensmittel-Untersuchung und-Forschung*, 138(2):75-80).

English language abstract of C100 (Hunziker et al., "High-pressure Liquid Chromatographie Determination of 5-Hydroxytryptamide in Coffee," *Mitteilungen aus dem Gebiete der Lebensmitteluntersuchung und Hygiene*, 1979, 70(1), pp. 142-152).

English language abstract of C101 (Hunziker, "Determination of 5-Hydroxytryptamide in Coffee Using High-Pressure Liquid Chromatography," 1977, *Mitteilungen aus dem Gebiete der Lebensmitteluntersuchung und Hygiene*, 68(2):267-274).

English language abstract of C127 (Koenig et al., "Gas Chromatography and Mass Spectrometry as Aids in Studying High-Boiling Coffee Compounds," Institut fur Organische Chemie und Biochemie, pp. 271-278; and Colloque Scientifique International sur le Cafe (1983), Volume Date 1982, $10^{th}$).

Urban, 1959, "Physiology of some flavonoids and oxycinnamic acid. II. Annual and diurnal periodicity of formation," *Planta*, 52:565-82.

Sciortino, 1969, *Bollettino Chimico Farmaceutico*, 107(8):506-11.

Acker, 1966, *Suesswaren*, 15(10):622-24, 626-68.

Szelag, 1984, *Przemysl Spozywczy*, 38(9):355-57.

Nagao, *Chemical and Pharmaceutical Bulletin*, 32(7)2687-99.

Sacher, 1965, *Zeitschrift fuer Lebensmittel-Untersuchung und-Forschung*, 128(5):264-67.

Mano, 1965, *Revista Portuguesa de Farmacia*, 15(3):398-401.

Martin, 1964, *Medicamenta*, 32(16):9-12.

Hahn, 1938, *Berichte der Deutschen Chemischen Gesellschaft*, 71 B 2175-82, 2183-91.

* cited by examiner

METHOD OF IDENTIFYING MODULATORS OF PP2A METHYLASE

CROSS-REFERENCE TO RELATED APPLICATIONS

This application claims the benefit of priority to PCT/US03/07658, filed Mar. 13, 2003, which claims priority to U.S. provisional application No. 60/363,537, filed Mar. 13, 2002. The entire contents of each of these applications is incorporated herein by reference in its entirety.

STATEMENT REGARDING FEDERALLY SPONSORED RESEARCH OR DEVELOPMENT

This invention was made with government support under Grant Number GM061284, awarded by the National Institutes of Health ("NIH"). The U.S. government has certain rights in the invention.

BACKGROUND

A variety of diseases are characterized partly by alteration in the pattern or amount of phosphate in regulatory or structural proteins. Protein phosphate content generally is controlled by phosphate addition, which is catalyzed by kinases, and by phosphate removal, which is catalyzed by phosphatases. Whereas kinases most often are regulated with great specificity, protein phosphatases are characteristically less selective. Thus, whereas kinases generally trigger systemic events in response to rather singular, specific stimuli, and then generally do so only through one signaling pathway, phosphatases exhibit broad dephosphorylating activity toward many of the phosphoproteins in their environment. Because of their specificity, kinases have always seemed especially attractive targets for drug development. For exactly the same reason, phosphatases, because of their lack of selectivity and broad systemic activities, have been viewed unfavorably as drug development targets.

Nevertheless, a number of attempts have been made to use phosphatase modulators for therapeutic purposes. For instance, Schieven in U.S. Pat. Nos. 5,565,491 and 5,693,627 reports on the use of phosphotyrosine phosphatase inhibitors to control proliferation of immune B cells. The patents disclose inhibitors that act directly on the phosphatase: metal-organic coordinate covalent compounds, nonhydrolyzable phosphotyrosine analogs, the *streptomyces* protein phosphatase inhibitor Dephostatin, and the prostatic acid phosphatase inhibitor 4-(fluoromethyl)phenyl phosphate. The inhibitors, as disclosed in the patents, inhibited proliferation of B cell leukemia and lymphoma cells, but also inhibited proliferation of normal B cells.

Lazo et. al. in U.S. Pat. Nos. 5,700,821, 5,856,506, and 5,925,660 discloses synthetic phosphatase inhibitors produced by combinatorial synthesis using L-glutamic acid as the initial scaffold. As disclosed in the patents, the compounds inhibited a variety of protein phosphatases, including PP1, PP2A, PP3, CDC25A, and CDC25B, and inhibited proliferation of human breast cancer cells in culture.

Hemmings discloses in U.S. Pat. No. 6,159,704 modulation of the phosphatase activity of the catalytic subunit of PP2A ("PP2Ac") via its interaction with eRF1. As disclosed, eRF1 is the ribosome-associated factor responsible for polypeptide chain release at the termination of protein synthesis; but, it also binds to and interacts with the catalytic subunit of PP2A. According to the disclosure, eRF1 recruits PP2A to the ribosome and mediates the role of PP2A in protein synthesis. According to the patent, the inhibitors disrupt the interaction between eRF1 and PP2Ac. As further disclosed in the patent, they, thus, might inhibit protein synthesis, and therefore, might be useful to reduce aberrantly high protein synthesis and cell proliferation which, accordingly, might make them useful for treating proliferative disorders.

Yet another example in this regard is disclosed by Honkanen et. al. in U.S. Pat. No. 5,914,242. As disclosed in the patent, inhibitors of certain serine/threonine protein phosphatases, in particular fostriecin, an organic compound first isolated from *streptomyces*, is used to reduce damage to the heart following myocardial infarction. According to the patent, fostriecin inhibits PP2A thereby causing greater phosphorylation of the protein 1-2. This leads to proteolysis of 1-2 and reduces its level in the cell, because the phosphorylated protein is a much more active substrate for the protease. Since 1-2 inhibits PP1, the decrease in 1-2 activity due to proteolysis results in increased PP1 activity. According to the disclosure, increased PP1 activity protects cells from the deleterious effects of ischemia, although the mechanism of protection is not known. Further according to the disclosure, the protective effect of fostriecin might be due to inhibition of phosphatase activity that results in less dephosphorylation of proteins phosphorylated by protein kinase C.

The inhibitors in all of the foregoing patent disclosures, except Honkanen, act directly on the phosphatase, inhibiting its activity competitively or irreversibly. The inhibitor disclosed by Honkanen acts specifically to disrupt the interaction of the phosphatase, PP2Ac, with a ribosomal protein and likely will affect primarily the action of PP2Ac on protein synthesis, rather than its more general action as a phosphatase. In any case, all of the inhibitors of the foregoing patents act solely to decrease the activity of phosphatases. Inherently they cannot act to increase phosphatase activity, although, this is desirable in many cases.

Alzheimer's Disease (AD) is a progressive neurodegenerative disease associated clinically with memory impairment and decreased cognitive function [Selkoe, 2001 #2]. Postmortem brains of AD patients display two pathological hallmarks: neuritic plaques and neurofibrillary tangles (NFTs). The plaques are extracellular deposits. They are composed of amyloid b-protein (Ab), which is a peptide derived from proteolytic cleavage of the amyloid precursor protein. NFTs, in contrast, are found primarily within the cell body. They are composed, in large part, of filaments of tau protein.

Tau normally is found predominantly in the axons of neurons where it stabilizes microtubules (MTs) and promotes their polymerization [Buee, 2000 #3]. MTs play a major role in maintaining the cellular architecture of neurons and are largely responsible for axonal transport [Goldstein, 2000 #4]. The integrity of MT structure is therefore critical for proper neuronal function and synaptic transmission. While tau normally is phosphorylated, it is abnormally hyperphosphorylated in NFTs [Grundke-Iqbal, 1986 #47]. Increased phosphorylation appears to precede and promote NFT formation [Alonso, 2001 #5] [Alonso, 1996 #10]. Hyperphosphorylated tau is also found in the cytobsol of NFT-containing neurons [Kopke, 1993 #49]

Phosphorylation inhibits tau's ability to bind and stabilize MTs [Bramblett, 1993 #7] [Biernat, 1993 #8] [Alonso, 1994 #9]. Furthermore, hyperphosphorylated tau has a dominant negative effect in that it promotes MT disassembly by binding normal tau, MT associated protein 1, and MT associated protein 2, interfering with the ability of these three proteins to stabilize MTs [Alonso, 1997 #48]. These effects help account for the observation that neurons containing NFTs lack MTs.

The cytoskeletal disruption brought about by hyperphosphorylated tau thus provides an explanation for its role in the neurodegeneration associated with AD.

Genetic evidence supports the conclusion that a critical event in the development of AD-type dementia is tau hyperphosphorylation [Lee, 2001 #6]. Though under some conditions Ab accumulation has been shown to promote NFT formation [Lewis, 2001 #11] [Gotz, 2001 #12], plaque formation is not essential for NFT-associated dementias, the so-called 'tauopathies'. Mutations in the tau gene underlie several familial neurodegenerative diseases where filamentous deposits of hyperphosphorylated tau have been observed in the absence of amyloid plaques, most notably fronto-temporal dementia and Parkinsonism linked to chromosome 17 [Lee, 2001 #6].

Tau hyperphosphorylation results from an imbalance between kinase and phosphatase activities. Phosphorylation is catalyzed by the neuronally enriched serine/threonine kinases glycogen synthase kinase 3b (GSK-3b) and cyclin-dependent kinase 5 (CDK5) [Buee, 2000 #3] [Billingsley, 1997 #13]. The most important tau dephosphorylating enzyme is protein phosphatase 2A (PP2A) [Planel, 2001 #14] [Merrick, 1997 #15] [Kins, 2001 #16] [Gong, 1994 #50].

Recent results suggest that a decrease in PP2A activity, rather than increased kinase activities, is crucial for the elevated levels of tau phosphorylation associated with NFT formation. PP2A expression has been found to be significantly reduced in the hippocampus of AD brains relative to control brains [Vogelsberg-Ragaglia, 2001 #17], and expression studies in mouse brain indicate a general decrease in PP2A expression levels with age [Jiang, 2001 #18]. Treatment of cultured human neurons with the PP2A inhibitor okadaic acid results in tau hyperphosphorylation, reduced binding of tau to MTs, MT depolymerization, and axonal degeneration [Merrick, 1997 #15]. Moreover, starved mice display a pattern of tau hyperphosphorylation similar to that found in AD brains [Planel, 2001 #14], and this hyperphosphorylation appeared to result from decreased PP2A activity towards tau rather than an increased kinase activity. In fact, the tau phosphorylating activities of CDK5 and GSK-3b decreased under these conditions. Thus, reduced PP2A activity towards tau must be part of any model accounting for NFT formation during the progression of AD.

PP2A is a multimeric protein complex consisting of a 65 kDa A subunit that acts as a scaffold for the association of a 36-kDa catalytic C subunit and one of a variety of regulatory B subunits [Janssens, 2001 #19]. B subunits control the substrate specificity and subcellular localization of PP2A. Ba, the major regulatory subunit in brain [Kamibayashi, 1994 #20], targets trimeric PP2A to MTs [Sontag, 1995 #21] and dramatically increases the enzyme's activity towards the tau protein [Sontag, 1996 #22]. ABaC heterotrimers bind directly to the carboxyl-terminal MT binding domain of tau [Sontag, 1999 #23]. The highly conserved carboxyl-terminal sequence of the PP2A C subunit is a focal point for the enzyme's regulation. Reversible methyl esterification of the C-terminal leucine a-carboxyl group of the PP2A C subunit is a major locus of control [Tolstykh, 2000 #26] [Wu, 2000 #27] [Yu, 2001 #28] [Wei, 2001 #29].

PP2A methylation is controlled by a specific S-adenosyl-methionine (SAM) dependent methyltransferase [Lee, 1993 #24] and a specific methylesterase [Lee, 1996 #25]. Methylation modulates PP2A activity by controlling the association of regulatory B subunits with the catalytic AC core [Tolstykh, 2000 #26] [Wu, 2000 #27] [Yu, 2001 #28] [Wei, 2001 #29]. The assembly of ABC heterotrimers proceeds as a multistep process with AC dimer methylation followed by binding of regulatory B subunits (FIG. 1). Tolstykh et al. [Tolstykh, 2000 #26] demonstrated that methylation of AC dimers from bovine brain dramatically increases their affinity for Ba regulatory subunits. Given the critical role of Ba in targeting PP2A activity towards tau, a decrease in PP2A methylation could lead to tau hyperphosphorylation, NFT formation, and neurodegeneration.

Decreased PP2A activity can contribute not only to tau hyperphosphorylation, but it can lead to other clinical indicators. For instance, homocysteine, through SAH hydrolase, is an end product of SAM-dependent methylation. The hydrolase reaction is reversible, and actually favors condensation of homocysteine and adenosine to form SAH (S-adenylhomocysteine). SAH is a potent inhibitor of methylation and accumulation of homocysteine (Hcy) thus generally is accompanied by increased SAH and, consequently, is associated with decreased methylation activity. Therefore, high plasma homocysteine levels generally may be indicative of decreased protein methylation and resultant decreases in methyl-dependent protein activities, such as PP2A phosphatase.

Indeed, over the last several years data has emerged in the clinical literature demonstrating a significant correlation between elevated plasma homocysteine (Hcy) and the occurrence of AD [Seshadri, 2002 #1] [McCaddon, 1998 #30] [Clarke, 1998 #31]. Elevated plasma Hcy has long been established as an independent, graded risk factor for cardiovascular disease [Clarke, 1991 #32] [Boushey, 1995 #33] [Welch, 1998 #34]; but, its role in AD has taken longer to establish. An early study found that patients with pathologically confirmed AD had significantly elevated plasma Hcy levels relative to a control group [Clarke, 1998 #31]. Hcy levels in the AD patients remained stable over time even as the disease progressed, suggesting that the elevation was not a result of neurodegeneration. Furthermore, patients with high plasma Hcy displayed more rapid neural atrophy over the course of three years than did patients with lower levels. More recent data from a prospective study provides convincing evidence that a rise in plasma Hcy precedes the onset of AD and is an independent risk factor for the disease [Seshadri, 2002 #1]. Baseline plasma Hcy levels were measured in 1092 non-demented patients and the occurrence of AD in this group was followed for several years. After adjusting for other AD risk factors, the authors found that plasma Hcy levels greater than 14 micromolar coincided with a roughly two-fold increased risk of developing AD. Further, elevated plasma Hcy appears to be a graded risk factor, with a 40 percent increased risk of developing AD associated with each 5 micromolar incremental rise. These studies clearly indicate a connection between high plasma Hcy and AD. While it has been recognized that insight into the mechanism underlying the association could give important clues for treatment of the disease, recognition of the association thus far has not provided a better understanding of AD or any other disease.

Elevated plasma homocysteine has been established as a risk factor not only for AD but also for heart disease, Type 2 diabetes, obesity, multiple sclerosis, stroke, cancer, rheumatoid arthritis, vascular disease, and birth defects; as well as various neurological illnesses including, among others, Parkinson's, depression, schizophrenia, and alcoholism. The relationship between elevated serum homocysteine and underlying disease etiology has not been elucidated for any of these diseases. Perhaps because of this, establishing the link has not led to effective therapeutic modalities, as yet. The general situation for all the diseases in this regard is fairly well illustrated by the foregoing discussion relating to Alzheimer's Disease. Presently nutritional supplementation is the only intervention thus far available for altering plasma homocysteine levels, and thereby, perhaps, reducing risk factors for these diseases. Unfortunately, whatever the efficacy of nutritional intervention at reducing plasma homocysteine, there is no evidence as yet that nutritional intervention actually reduces the homocysteine associated risk factor for disease. Furthermore, nutritionally forced reductions in plasma homocysteine actually may have deleterious effects.

Clearly, there is a need for an improved understanding of: the link between homocysteine levels, disease risk factors and disease itself, its etiology, and the factors that control the development and progress of the diseases. Even more important and pressing is the need for better diagnostic tools and for, above all, effective therapies for AD. Unfortunately, AD is merely illustrative in this regard. Many other diseases also are poorly understood, hard to diagnose, and presently lacking effective treatments.

Heretofore, proteins such as PP2A did not seem promising targets for effective therapeutics. Typically, they are ubiquitous, abundant and, perhaps worse for drug development, they are important general regulators of protein phosphokinase or protein phosphatase activities that affect virtually all phosphoproteins, and they interact with a very wide range of regulatory proteins. Thus, It appeared likely that targeting them would only lead to general systemic distress. Furthermore, it seemed likely that modulators of phosphatase activity would suffer some of the same disadvantages as the inhibitors discussed above. These inhibitors disadvantageously target a broad spectrum of serine/threonine proteases involved in regulating and performing vital cell processes and, consequently, broadly affect cellular metabolism and physiology, often with undesirable or deleterious consequences. Given their similar ubiquity and regulatory role, the same disadvantages were expected to limit the usefulness and efficacy of agents that modulate the activities of phosphatases. Thus, there has been and there continues to be a real need for improved diagnostics, better agents for altering the activities of proteins important in disease process, and effective methods for treating disorders and diseases such as AD.

SUMMARY OF THE INVENTION

The present invention, in part to overcome these problems provides among other things as follows.

A method for identifying a compound for altering a protein activity, comprising: identifying a compound that modulates methylation of a protein phosphatase that affects a protein activity and determining that the protein activity is altered by modulating with the compound methylation of the protein phosphatase. In particularly preferred embodiments in this regard the protein phosphatase is a PP2A protein phosphatase. In another regard in certain of the preferred embodiments in the protein activity is the phosphate level of a phosphorylated protein. In certain highly preferred embodiments in these and other regards the protein activity is phosphorylation of tau. In especially highly preferred embodiments in these and other regards tau is hyperphosphorylated, and the compound increases methylation of PP2A and decreases tau hyperphosphorylation.

In another aspect, certain preferred embodiments of the invention provide methods for identifying a composition for altering a protein activity, comprising: identifying a composition that modulates methylation of a protein phosphatase that affects a protein activity, using the composition to modulate methylation of the phosphatase, and determining that modulating phosphatase methylation alters the protein activity. In certain aspects of the invention in this regard, in certain of the preferred embodiments, the composition is an extract of a natural product. In further preferred embodiments in this regard the composition is an extract of a traditional medicine. In another preferred aspect of the invention in these and other regards, the protein phosphatase is a PP2A protein phosphatase. In a particular aspect of the invention further in these regards, in certain of the preferred embodiments the protein activity is tau phosphorylation. In especially highly preferred embodiments in this regard, tau is hyperphosphorylated, the compound increases methylation of PP2A and decreases tau hyperphosphorylation.

The invention further provides in certain aspects and preferred embodiments, compounds for altering protein activity, wherein the compounds are identified by a method comprising: identifying a compound that modulates methylation of a protein phosphatase that affects a protein activity and determining that the protein activity is altered by modulating with the compound methylation of the protein phosphatase. In particularly preferred embodiments in this regard the protein phosphatase is a PP2A protein phosphatase. In another regard in certain of the preferred embodiments in the protein activity is the phosphate level of a phosphorylated protein. In certain highly preferred embodiments in these and other regards the protein activity is phosphorylation of tau. In especially highly preferred embodiments in these and other regards tau is hyperphosphorylated, and the compound increases methylation of PP2A and decreases tau hyperphosphorylation. The invention further provides compositions comprising the compounds. In addition, the invention provides methods for treating cells to alter therein an activity of a protein, comprising administering to the cells by an effective route and/or in an effective amount a compound in accordance with the invention and/or a composition comprising a compound in a accordance with the invention.

In yet another aspect of the invention, certain of the preferred embodiments provide compounds and/or compositions for altering a protein activity, wherein the compound is identified by a method comprising identifying a compound and/or a composition that modulates methylation of a protein phosphatase that affects a protein activity, using the composition to modulate methylation of the phosphatase, and determining that modulating phosphatase methylation alters the protein activity. In another regard in certain of the preferred embodiments in the protein activity is the phosphate level of a phosphorylated protein. In another preferred aspect of the invention in these and other regards, the protein phosphatase is a PP2A protein phosphatase. In a particular aspect of the invention further in these regards, in certain of the preferred embodiments the protein activity is tau phosphorylation. In especially highly preferred embodiments in this regard, tau is hyperphosphorylated, the compound increases methylation of PP2A and decreases tau hyperphosphorylation. In certain aspects of the invention in these and other regards, in certain of the preferred embodiments, the composition is an extract of a natural product. In further preferred embodiments in this regard the composition is an extract of a traditional medicine. In these regards, further, in certain aspects the invention provides in certain of the preferred embodiments methods for treating cells to alter therein an activity of a protein, comprising administering to the cells by an effective route and/or in an effective amount a compound in accordance with the invention and/or a composition comprising a compound in a accordance with the invention. In particularly preferred embodiments in this regard, in accordance with certain aspects of the invention, the compound and/or composition is derived from a natural product, it affects methylation of PP2A and decreases tau hyperphosphorylation and it is administered to patients suffering from AD.

DESCRIPTION

Figure 1:
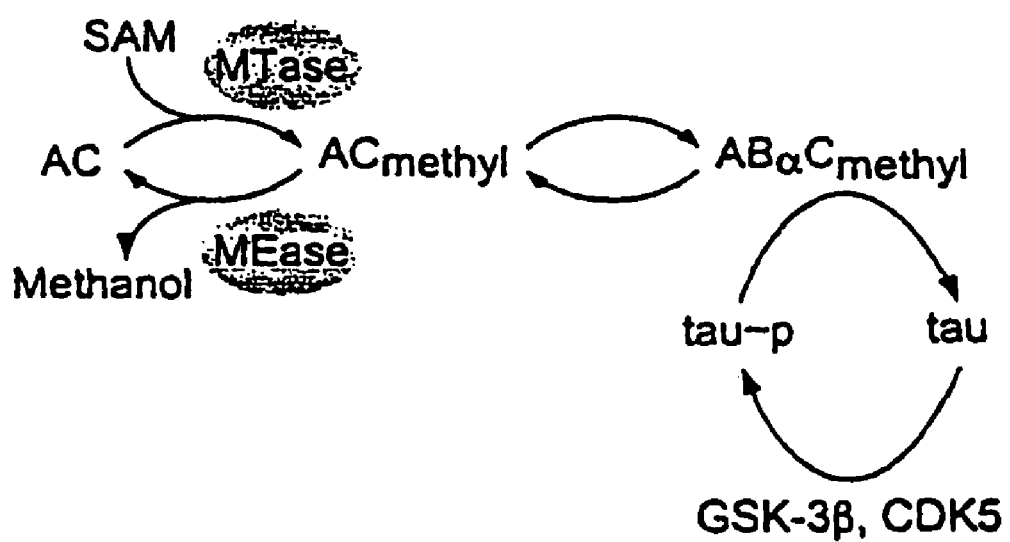
FIG. 1 is a schematic diagram illustrating processes involved in PP2A methylation and tau phosphorylation. As illustrated in the figure: (a) PP2A methyltransferase (MTase) (also referred to as PPMT) binds to and methylates AC dimers (AC and ACmeth); (b) a methylesterase (MEase) (also referred to as PPME) catalyzes the reverse reaction and removes methyl groups; (c) methylation of AC dimers dramatically increases their affinity for Ba subunits, resulting in increased formation of ABaCmeth trimers; (d) the ABaC[meth] timer is the major tau phosphatase activity in vivo; (e) whereas phosphorylation appears to be controlled primarily by GSK-3b and CDK5. Increased methylation of PP2A AC dimers leads to increased amounts of ABaCmeth, increased phosphatase activity and decreased levels of tau phosphorylation. (SAM: S-adenosylmethionine)

The key regulatory roles of protein kinases and protein phosphatases are well known. Enzymes of both types have been and continue to be the primary drug development targets. Although these efforts have met with some success, they have not produced, as yet, many hoped for advances. The invention herein disclosed in certain of its preferred aspects and embodiments relates to bioactive agents and methods for modulating the activity of regulatory enzymes, such as kinases and phosphatases, without incurring difficulties that have been encountered with other approaches.

Bioactive agents that act directly on key kinases and phosphatases, at least at present, generally act as inhibitors, and their effects do not discriminate among the varied activities of these enzymes, which generally carry out a variety of regulatory functions. Furthermore, the effects of the agents cannot be calibrated with precision. Consequently, direct-acting inhibitory agents too often not only reduce the unwanted activity but also, by the same action, alter the activity to another aberrant level that also is deleterious.

Preferred embodiments in some aspects of the present invention augment direct targeting agents and methods for modulating the activities of enzymes, such as regulatory enzymes, especially key regulatory enzymes, and overcome some of their disadvantages. In this regard, in certain aspects of the invention, the preferred embodiments relate to regulatory enzymes that are kinases or are phosphatases, especially key regulatory kinases and phosphatases, and kinases and phosphatases that are important determinants of dysfunction and disease.

In further preferred aspects and embodiments in these and other regards, the invention relates to indirect targeting for modulating the activities of enzymes, including regulatory enzymes, especially kinases and phosphatases, particularly kinases and phosphatases that play a key regulatory role, and those that are important determinants of dysfunction and disease. In certain highly preferred aspects of the invention in preferred embodiments thereof the invention provides methods to modulate the activities of target enzymes by acting, partly or entirely, on other, secondary targets that regulate the activity of the primary target. In certain highly preferred embodiments of the invention in this regard, the secondary targets naturally regulate the primary target. Further, in preferred embodiments in this regard, the secondary targets exert incremental regulatory control on the primary targets. Agents in accordance with this aspect of the invention thereby are useful to exert incremental control of the activity of the secondary target, thus allowing relatively fine control over the primary target activity. In still further preferred aspects of the invention, the preferred embodiments provide both positive and negative regulatory control of the primary target. In other aspects of the invention in this regard, the preferred embodiments provide positive regulatory control (stimulatory rather than inhibitory). Further preferred embodiments provide various combinations of these aspects and embodiments of the intention.

In these regards and others, the preferred embodiments in certain preferred aspects of the invention relate to the activities of primary target enzymes regulated by post-translational modifications and to modulating the activities of enzymes that effectuate the post-translational modifications and thereby regulate the activity of the primary target(s).

These and other aspects of the invention are illustrated by particularly preferred embodiments relating to the phosphatase PP2A, which plays a central regulatory role in a variety of cell processes, and to PP2A methyltransferases and methylesterases which, respectively, methylate and demethylate a specific site in a PP2A subunit. Methylation increases formation of the active PP2A trimer, thus promoting PP2A phosphatase activity. Demethylation leads the system back toward the other side of the equilibrium, reducing the amount of active PP2A, thus decreasing PP2A phosphatase activity. Illustrative of other preferred embodiments of the invention in this regard, the present invention provides for both up regulating and down regulating PP2A phosphatase activity, through agents that act, respectively, on PP2A methyltransferase and PP2A methylesterase.

The same approach can be applied to modulate the activities of other enzymes, including among others, kinases and phosphatases. Other activities regulated by methylation also can be controlled through methyltransferase and methylesterase activities, much the same as described for PP2A above. Still other activities, not regulated by methylation, but subject to regulatory control by other post-translational modifications can be modulated in much the same way with the other modifications as for the methylation control enzymes discussed above.

The invention thus relates both to methods for controlling primary target activities, preferably of primary target enzymes, by effecting control over the activity of a secondary target activity that controls the activity level of the primary target. It relates further in this regard to agents for effecting the control, to methods of or for identifying candidate agents, to methods for verifying the candidates, and for optimizing the agents. It relates as well in these regards and others to compositions and methods for using the agents to regulate activities in vitro, in cells in culture, in physiological models, in model organisms, and in treating disorders and disease.

Furthermore, the invention relates not only to modulating the activity of a primary target in accordance with the foregoing, but also to the effect of regulation on substrates of the primary target. An example discussed elsewhere herein in greater detail is illustrative in this regard. In this example, an agent that inhibits PP2A methylesterase is administered. PP2A methylation affects primarily Ba-containing PP2A trimers, which are located primarily in brain and liver. Therefore, the agent will act to increase PP2A phosphatase activity in brain, inter alia. In Alzheimer's Disease decreased PP2A phosphatase activity is associated with marked increase in tau phosphorylation, and hyperphosphorylated tau is an important component in the neurodegenerative processes that underlie the disease. The agent, by decreasing demethylation and thereby increasing PP2A phosphatase activity, concomitantly decreases tau hyperphosphorylation and ameliorates disease symptoms. The same end result in accordance with the invention can be accomplished with a variety of other systems involving other primary target enzymes, other secondary enzymes, and different post-translational modifications.

In accordance with these and other aspects of the invention, the secondary targets, exemplified above by PP2A methyltransferase and PP2A methylesterase, provide novel targets for high throughput screens for agents that can be used not only to regulate the activities of the secondary targets themselves, but also thereby the activity of primary targets. Agents that act on the secondary targets thereby effect control and/or to modulate the activity or occurrence of a disorder and/or disease associated and/or causative factor. The invention in this regard further relates in certain of its preferred aspects and embodiments to formulations of such agents for diagnosis and treatment uses. Further, it will be noted that in accordance with further preferred embodiments of the invention, PPMS (PP2A methylation status) defects are detected that are critical early steps in the development of a disorder and/or disease and that, in especially preferred embodiments in this regard, occur well before the onset of most other symptoms. The opportunity for very early intervention, thus provided by the invention, enhances agents and therapies that target the PP2A methylating and demethylating enzymes in accordance with other aspects of the invention herein discussed and provides thereby the best avenue to effective preventative and therapeutic protocols for diseases that currently lack effective treatments.

In certain particularly highly preferred aspects of the invention in this and other regards, certain preferred embodiments of the invention relate to PP2A, to PP2A comprising methyl-accepting subunits, to the activities and physiological effector functions of PP2A and to the modulation of one or more PP2A physiological activities to maintain health, to prevent disorders and/or disease, to treat disorders and/or disease, and to ameliorate and/or eliminate adverse symptoms of disorder and/or disease. In particular, the invention relates to PP2A phosphatase activity and its effect on specific phosphoproteins, especially phosphoproteins regulated by phosphorylation and/or by dephosphorylation, most particularly those that play an important role in maintaining health and/or in the development of disorders and/or disease.

In a particular aspect in this regard, the invention relates to the modulation of PP2A activity, to the modulation thereby of PPMS, to the modulation of phosphoprotein phosphatase activity thereby, and to the methyltransferase and methylesterase enzymes that control PPMS, including, among others, agents that facilitate methylation of PP2A or that inhibit demethylation of methylated PP2A. In addition, the invention relates to the identification of factors that ameliorate defects in PPMS, particularly those that mimic the effects on PP2A phosphatase activity of PP2A methylation, especially those that activate PP2A phosphatase activity, particularly PP2A phosphatase activity towards hyperphosphorylated proteins that, when hyperphosphorylated, cause aspects of disorder and/or disease, including, in particular, the microtubule-associated protein, tau, which, when hyperphosphorylated is a causative agent of neurodegeneration and mental illness, among others, often associated with AD.

The invention further relates in this and other regards to formulations for administering the aforementioned agents to subjects to increase methylation and activity of PP2A such as formulations that increase methylation and PP2A dephosphorylation activity toward hyperphosphorylated proteins, particularly proteins that exhibit hyperphosphorylation in disorder or diseased physiological states but not in healthy states, such as, in one very highly preferred embodiment in this regard, hyperphosphorylated tau protein associated with onset of Alzheimer's Disease and/or with the disease itself.

In these and other regards, the invention provides agents, formulations, and treatment strategies for the amelioration of PPMS deficiencies so that individuals can arrest, retard, or reverse the development of the aforementioned diseases. In this regard, in certain particular aspects and embodiments, the invention provides agents, formulations, and treatments for familial defects in metabolism or metabolic regulation that cause disease by increasing protein phosphorylation or preventing protein dephosphorylation by providing methods to modulate PP2A phosphoprotein phosphatase activity toward critical phosphoprotein substrates that cause disease, such as hyperphosphorylated tau protein.

Indicators, Metrics, and Diagnostics

Furthermore in accordance with the invention herein disclosed, aspects of methylation metabolism and PP2A methylation provide quantitative and qualitative diagnostic markers of disease risk, early indications of disease development, and the presence of disease. The invention relates in this regard to, among other things, methods for assessing, measuring, determining, assaying, and the like, PP2A phosphoprotein phosphatase activity and PPMS, particularly in clinical samples, and to methods of diagnosis and prognosis based on these assessments, measurements, determinations, assays, results, etc.

Accordingly, the invention provides methods to assess PPMS and determine PPMS predictive or indicative of disorder or disease, particularly states or conditions that lead to the aforementioned diseases, especially those that are life threatening. Homocysteine level is one such metric that provides a useful parameter for risk assessment in this regard, not only of previously known diseases such as heart disease and AD, but also other diseases that involve characteristic alterations of PP2A methylation. In addition, the invention further provides measures of methylation metabolism that are more direct than plasma homocysteine levels and provide more reliable and more cost effective determinations of PP2A methylation status (PPMS) and PP2A activity than serum homocysteine measurements. The independent measures of methylation metabolism and PPMS provided by the present invention overcome disadvantages of the standard techniques for homocysteine serum determination.

Figure 2:
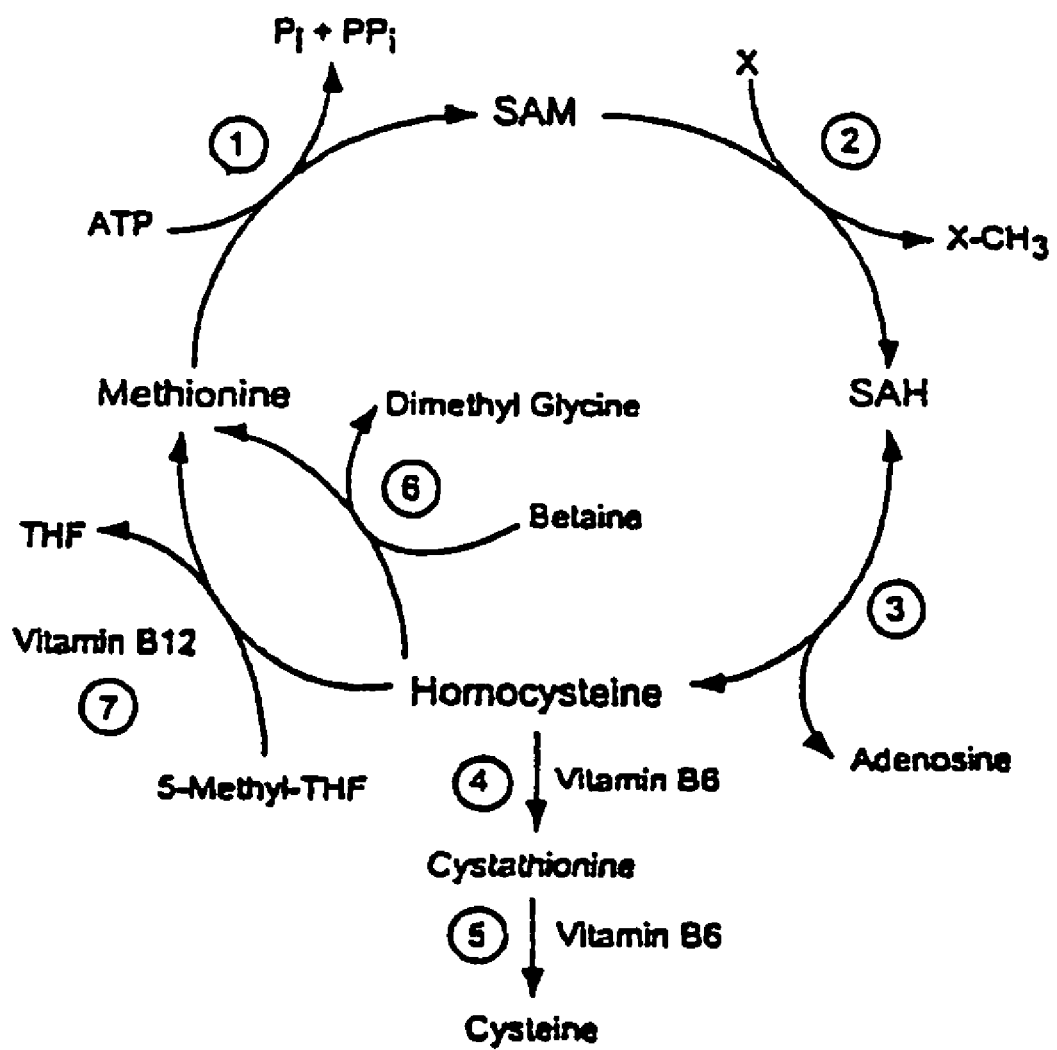
FIG. 2 is a schematic diagram of key steps and enzymes in the methyl cycle. Enzymes are indicated by circled numbers as follows: (1) methionine adenosyltransferase; (2) SAM-dependent methyltransferases; (3) SAH hydrolase; (4) cystathionine b-synthase; (5) cystathionine g lyase; (6) betaine homocysteine methyltransferase; (7) methionine synthase.

Notably in this regard, for example, homocysteine is central to the methyl cycle (FIG. 2) and plays an important role in cellular methylation [Selhub, 1999 #35] [Scott, 1998 #36] [Finkelstein, 1998 #37]. SAM-dependent methylation reactions result in the production of S-adenosylhomocysteine (SAH) (reaction 2), which is subsequently cleaved by the enzyme SAH hydrolase to adenosine and homocysteine (reaction 3). The SAH hydrolase reaction is reversible with the equilibrium actually favoring the condensation of homocysteine and adenosine to form SAH. SAH is a potent competitive inhibitor of virtually all methyltransferase enzymes and accumulation of Hcy is associated, via an increase in SAH, with a global decrease in cellular methylation [Wang, 1997 #39] [Yi, 2000 #40] [Caudill, 2001 #41]. These results are consistent with the hypothesis that Hcy facilitates the progression of AD by inhibiting brain PP2A methylation. Decreased C subunit methylation will result in reduced ABaC heterotrimer formation leading to tau hyperphosphorylation, NFT formation, neurodegeneration, and dementia. Thus, PP2A methylation links elevated plasma Hcy and AD, and it therefore provides a more direct and more accurate assay of AD indicators in this regard than serum Hcy. The invention in this regard provides agents, formulations, and treatments for assessing and reducing the risks of the aforementioned diseases predicted by measurements of elevated plasma homocysteine (>10 micromolar).

The invention also provides in some aspects and embodiments novel methods for PPMS assessment that provide the first direct assays to assess the efficacy of agents, formulations, and treatments designed to ameliorate abnormalities, promote health, and prevent or retard the development of the aforementioned disease states. Preferred methods of the invention in this regard include measuring DNA hypomethylation in blood, measuring levels of S-adenosylmethionine and S-adenosylhomocysteine in blood and/or cerebrospinal fluid, measuring levels of adenosine, methionine, folate, and homocysteine in blood and/or cerebrospinal fluid, and measuring levels of protein N-methylation in hair or skin. In accordance with further aspects of the invention in this regard, PPMS defects are detected that are critical early steps in the development of these diseases, occurring well before the onset of most symptoms, thus allowing earlier diagnosis and interventions that are both more timely and, being more timely, also are more effective.

The Determination of PP2A Methylation and Demethylation

The invention provides several methods for detecting PPMS, directly, and for characterizing normal and abnormal PPMS in an organism, particularly in a human. A preferred method in this regard measures levels of PP2A methyl esterification in whole blood by immunoassay using antibody specific for methylated PP2A that does not significantly cross-react with unmethylated PP2A. Antibodies specific for methylated PP2A and other reagents and methods for use in immunoassays in this regard are described in Tolstykh et al., (2000); "Carboxyl methylation regulates phosphoprotein phosphatase 2A by controlling the association of regulatory B subunits;" EMBO J. 19: 5682-5691 [#26], which is herein incorporated by reference in its entirety in parts pertinent particularly to antibodies, reagents, and methods for determining the presence and extent of methylation of PP2A.

In addition to the aforementioned immunological assays, PP2A methylation and methylesterase activity can be determined by methanol release. PP2A can be incubated in mildly alkaline solution, which hydrolyzes the PP2A methyl ester, releasing methanol. After incubation to complete hydrolysis, methanol is measured by conventional techniques. Methylesterase-catalyzed PP2A demethylation is measured much the same way, but the methanol determined is that released by the methylesterase at neutral pH, not by alkaline hydrolysis. The released methanol at neutral pH is measured by the same standard procedures.

The results of PP2A methylation determinations in accordance with the foregoing methods, or other methods, provide an accurate assessment of PP2A activity, are diagnostic of PP2A insufficiency and, in some cases, of disease, and are used in accordance with the invention to diagnose disease, particularly at early stages, to assess the utility and likely effectiveness of interventions that affect PP2A methylation and activity, and to follow and assess the effects and efficacy of any such intervention undertaken, and of other treatment modalities as well. The information from these assays, alone or combined, provides, in accordance with certain particularly preferred embodiments of the invention in this regard, a clear view of PPMS and of genetic, behavioral, and/or nutritional components of a PPMS problem. Moreover, in accordance with these aspects and preferred embodiments of the invention, the results accurately indicate appropriate remedial treatment modalities and provide a monitor of efficacy throughout a course of treatment.

Identification of PPMS-Modulating Agents

In another aspect, in certain of its preferred embodiments, the invention further provides methods to identify and characterize agents to modulate PPMS. In certain preferred embodiments such agents are identified by screening methods using monoclonal antibodies that bind specifically to methylated, but not unmethylated PP2A.

Candidate modulators of PPMS can be screened using the PP2A methylation assays described above and in the examples. Purification procedures for PP2A methyltransferase and methylesterase, and additional assays, suitable for use in the invention in this regard, are described in Lee et al. (1996); A specific protein carboxylmethylesterase that demethylates phosphoprotein phosphatase 2A in bovine brain; Proc. Natl. Acad. Sci. U.S.A. 93: 6043-6047 [#25] and Lee et al. (1993); Protein phosphatase 2A catalytic subunit is methylesterified at its carboxyl terminus by a novel methyltransferase; J. Biol. Chem. 268: 19192-19195 [#24], which both are incorporated herein by reference in their entireties in parts pertinent particularly to the isolation, purification, assay, and use of the PP2A carboxylmethyltransferase and assay of PP2A methylation, in particular methylation by PP2A carboxylmethyltransferase.

As an initial screen, in accordance with certain preferred embodiments of the invention, candidate agents are added to mixtures containing PP2A, PP2A methyltransferase, and S-adenosylmethionine methyl donor. Following incubation, the level of PP2A methylation is assessed using the aforementioned antibody. Alternatively, in addition, methylesterified PP2A is mixed with the methylesterase and after a period of time the disappearance of methyl groups is assessed by the disappearance of the methylester epitope measured using the aforementioned antibody. In a further alternative approach, candidate agents are added to intact cells that express PP2A, the methylating enzyme, and the demethylating enzyme. Following a period of incubation, PP2A methylation is assessed. The impact of such treatments on PPMS is then directly assessed by measuring PP2A methylation by Western Blot analysis using the aforementioned antibodies.

In addition to the aforementioned immunological assays, methanol can be determined to measure PP2A methylation and demethylation, as described in examples set forth below. PP2A methylation is determined by incubating PP2A in mildly alkaline solution, which hydrolyzes the PP2A methyl ester, releasing methanol. After incubation to complete hydrolysis, methanol is measured by conventional techniques. Methylesterase-catalyzed PP2A demethylation is measured much the same way, but the methanol determined is that released by the methylesterase at neutral pH, not by alkaline hydrolysis. The released methanol at neutral pH is measured by the same standard procedures.

Genetic Markers

In a further aspect, the invention provides in certain preferred embodiments, methods for genetic analysis of aberrations that cause disease susceptibility, indicate likelihood of developing a deleterious hereditary condition of PPMS, and/or are predictive of treatment tolerance, side effects, and efficacy. Certain preferred embodiments in this regard relate to SNP(s) associated with alterations of PPMS, and to analysis of SNPs by standard techniques, such as specific probe PCR, LCR, RFLP, PCR-RFLP, and a variety of other methods useful both to discover and to determine SNPs. Also particularly preferred, in the certain aspects and embodiments of the invention in this regard, are DNA array analyses, including analyses to identify SNPs useful for diagnosis and prognosis in accordance with foregoing aspects of the invention, inter alia, particularly SNPs in genes that encode the following: protein kinases; more particularly, phosphoprotein phosphatases, most especially in this regard PP2A; enzymes that directly or indirectly modulate the activities of protein kinases; and, more particularly, enzymes that directly or indirectly modulate the activities of phosphoprotein phosphatases, particularly in this regard, methyltransferases and methylesterases, most especially in this regard PP2A methyltransferases and PP2A methylesterases.

EXAMPLES

Example 1

Methylation Assay in Partially Purified Extract Using 3H Incorporation

A cell-free extract is prepared from fresh mammalian brain tissue by homogenizing the tissue in Tris buffer, pH 7.5. The extract is clarified by centrifugation at 10,000×g for 30 min. Solid ammonium sulfate is added to the supernatant to 30% saturation and a clarifying precipitate is allowed to form for an hour. The solution then is cleared by centrifugation for 30 min at 10,000×g. The clarified supernatant is recovered and ammonium sulfate is added to 70% saturation. The resulting suspension is incubated overnight. Then the precipitate is collected by centrifugation at 10,000×g for 30 min. The resulting pellet is dissolved in Tris buffer, pH 7.5, and then further purified by DEAE ion exchange chromatography with stepwise elution. PP2A and the PP2A methylating and demethylating enzymes are eluted from the column in loading buffer containing 0.3 M NaCl.

PP2A methylating activity is assayed by 3H incorporation using S-Adenosyl[3H-methyl]methionine as substrate. An aliquot of the eluate is mixed with S-Adenosyl[3H-methyl] methionine and incubated under conditions favorable to methyltransferase activity. 3H-methyl-PP2A formed during the incubation is assayed by standard methanol procedures.

Example 2

Screening for Agents that Alter PP2A Methylation Using Partially Purified Extracts and H Incorporation Assays Extracts are prepared and purified and assays of PP2A methylation are carried out as described in the preceding example, except that compounds to be tested for effects on PP2A methylation also are added to the reactions. Effects of the compounds are scored relative to control assays.

Example 3

Cell-Based PP2A Methylation Assay

A cell tissue culture assay is also be employed. This screen is for drugs that cause increases in PP2A methylation in SY-SH5Y cells in the absence and/or presence of homocysteine. SY-SH5Y cells are grown to confluence in 36-well tissue culture plates. After the cells have reached confluence, the growth medium is supplemented with extracts prepared from medicinal herbs in the presence and absence of 200 pM homocysteine. After a suitable time (~3 h), cell proteins are extracted into 2% SDS, diluted, blotted onto PVDF or nitrocellulose membranes, and probed with monoclonal antibodies that recognize specific epitopes for either total or methylated PP2A. Extracts that increase methylation are identified as drug candidates for further study.

Example 4

Diets to Induce High Plasma Homocysteine in Mice

Male C57BL/J6 mice were obtained from the Jackson Laboratories (Bar Harbor, Me.) at 4 weeks of age. Mice were fed on a vitamin sufficient or a vitamin deficient diet for 9 weeks. All of the vitamin-sufficient diets contained folate, vitamin B6, and vitamin B12. All of the vitamin deficient diets lacked these vitamins. One group of mice was fed a vitamin deficient diet that had an enriched methionine content (Harlan Teklad TD97345). Another group was fed a vitamin deficient diet that contained basal levels of methionine (Harlan Teklad TD00428). The same was true for mice on the vitamin-sufficient diet. One group was fed a diet enriched for methionine (Harlan Teklad TD98002) and another was fed standard rodent chow 5001 c (Lab Diets). The mice were allowed free access to both food and water.

Example 5

Effects of Vitamin Deficiency on Body, Heart and Brain Weight of C57BUJ6 Mice

Wild type mice were placed on diets containing or lacking folate, vitamin B6, and vitamin B12 as described above for nine weeks. Brain and heart weights of mice in each group then were determined as follows. The brain was removed from each animal and frozen in liquid nitrogen prior to recording the weight. The heart was removed from each animal, perfused with approximately 10 ml of ice cold phosphate buffed saline, drained of buffer, and frozen in liquid nitrogen prior to recording the weight. Mice fed vitamin-deficient diets had dramatically decreased body and heart weights relative to mice fed vitamin supplemented diets, but not brain weight, as shown below.

Body, Brain, and Heart Weights for Mice Fed Diets with or without Folate, Vitamin B6, and Vitamin B12

|  | With Folate, $B_6 B_{12}$ | Without Folate, $B_6$ $B_{12}$ | With/Without |
|---|---|---|---|
| Body (g) | 25.9 ± 0.3 | 13.9 ± 0.4 | 1.87 |
| Heart (mg) | 115 ± 3 | 63 ± 2 | 1.83 |
| Brain (mg) | 397 ± 8 | 388 ± 5 | 1.02 |

Weights are reported ±standard error. N equals 30 for the diets with vitamins and 27 for the diets without vitamins.

Although the body and heart weights were dramatically reduced by the vitamin deficiencies, the brains appeared to be unaffected. This fits the idea that the brain is a privileged organ with a high priority for residual levels of folate and the B vitamins. One possible explanation is that the brain is somehow a high-priority organ and receives whatever precious folate and B vitamin resources are present. Although mice deficient for methylenetetrahydrofolate reductase have decreased amounts of 5-methyltetrahydrofolate in both brain and liver, the brain/liver ratio is over three-fold higher in null mutant mice [Chen, 2001 #51]. These data suggest that folate levels in the brain are maintained at the expense of other organs These results are similar to those obtained in previous research relating to the effects of vitamin deficiency on mice deprived of folate [Gospe, 1995 #52] and vitamin B6 [Bender, 1990 #57; Ha, 1984 #58]. Somewhat different results obtained in one study also are worth noting, however [Hofmann, 2001]. That study reported on the effects of elevated plasma Hcy on plaque formation in ApoE null mice (backcrossed ten generations into C57BUJ6 mice). The mice were four weeks old in that study, as in the present case, and they were fed the same four diets as used in this example, but for eight weeks rather then nine. However, that study found that the body weight of mice fed diets that contained folate, vitamin B6, and vitamin B12 after the eight weeks did not differ significantly from the body weight of mice fed on diets that lacked these vitamins.

Example 6

Determination of SAM and SAH

SAM and SAH levels were measured by high performance liquid chromatography (HPLC) according to the method described by Fu et al. in "Interrelations between plasma homocysteine and intracellular S-adenosylhomocysteine;" Biochem Biophys Res Commun 271: 47-53 (2000), which is incorporated herein by reference in its entirety particularly in parts pertinent to HPLC assays of SAM and SAH.

Samples of mouse brain were weighed and homogenized in two times weight/volume of 0.5 HClO4. Samples were centrifuged at 12,500 g for 5 min and the supernatant was filtered through a 0.22 mm membrane. Aliquots of 25 ml were injected and run on a hypersil 5 mm particle size, c18 (ODS), 250×4.6 mm (Phenomenex) column with an isocratic elution at 1.3 ml/min. The mobile phase consisted of 0.10 mM sodium acetate, 2.4 mM heptanesulfonic acid, 4.2% acetonitrile, and 50 mM sodium perchlorate. The pH was adjusted to 3.5 with 70% perchloric acid.

The retention times for SAM and SAH are 23 min and 29 min, respectively. Standards were run at five different concentrations: 10,000, 5,000, 2,000, 1,000, and 500 pM for SAM, and 10,000, 5,000, 1,000, 100, and 50 µM for SAH. Linear curves, obtained from the SAM and SAH standards, were used to calculate concentrations of SAM and SAH in the brain homogenates.

Example 7

Determination of Plasma Homocysteine

Homocysteine was measured by HPLC in serum samples reduced with tri-n-butylphosphine.

Serum was prepared from whole blood, which was allowed to clot for 30 min on ice and then centrifuged. Samples were aliquoted, snap frozen and stored at −80° C. for analysis. For analysis, 150 ml of serum was thawed and reduced in a mixture containing 50 ml of 0.1 M potassium borate, 2 mM EDTA, pH 9.5, 0.2 mM mercaptopropionylglycine, and 20 ml of 100 ml/l of tri-n-butylphosphine in dimethylformamide. The reduction was allowed to proceed for 30 min on ice after which samples were mixed with 125 ml of 0.6 M perchloric acid containing 1 mM EDTA and allowed to react at room temperature for 10 min, and then centrifuged at 15500 g for 10 min. 100 ml was withdrawn from the middle of the supernatant and mixed with 200 ml of 0.2M potassium borate, pH 10.5, containing 5 mM EDTA. 100 ml of 1.0 gm Ammonium 7-fluorobenzo-2-oxa-1,3-diazole-4-sulphonate/I.OL 0.2M potassium borate, pH 9.5, was added and the mixture incubated at 60° C. for 60 min. Samples were cooled and then analyzed using HPLC. 10 ml of derivatized sample was used for each injection. Buffer A (0.1 M acetate buffer, pH 4.0, containing 20 ml/l methanol) and Buffer B (0.1 M acetate buffer, pH 6.0, containing 50 ml/l methanol) were run at a flow rate of 1.0 ml/min from A to B over 12.5 min then 2.5 min of B, a 3.0 min gradient back to A and 2.0 min A before next injection. A standard was also analyzed to quantify values of homocysteine. Mercaptopropionylglycine was added to the reduction buffer as an internal standard to monitor any potential loss during reduction.

Example 8

Effects of Diet on SAM, SAH, Hcy and Methylation Rate

Mice were fed on diets containing or deficient in folate, vitamin B6 and B12 as set out above. SAM, SAH and Hcy were determined as described above.

Brain SAM levels were slightly higher in mice fed on the vitamin deficient diets than mice fed the normal diets. Plasma Hcy and brain SAH were substantially increased in mice fed the vitamin-deficient diets, compared to mice on the normal diet. The increases in SAH cause the methylation index (SAM/SAH) [Cantoni, 1978 #53] to be severely depressed, which reduces the overall methylation rate. The reduction in methylation rate caused by elevated SAH, may be the reason that SAM levels are elevated under nutrient conditions where SAM synthesis would be expected to be reduced.

Status of Methylation Metabolism in Mice Fed Diets with or without Folate, Vitamin B6, and Vitamin 812

| | Folate: $B_6$, $B_{12}$ | |
|---|---|---|
| | With | Without |
| Hcy (pM) | 20.8 ± 2.7 | 371 ± 64 |
| SAM (nmol/g) | 13.3 ± 1.0 | 17.0 ± 1.3 |
| SAH (nmol/g) | 1.7 ± 0.4 | 16.7 ± 4.4 |
| SAM/SAH | 10.0 ± 1.8 | 1.8 ± 0.8 |

Values are reported ±standard error. N=7 for the Hcy value given for mice fed a vitamin-deficient diet, while N=6 for all other values.

Example 9

Determination of PP2A Methylation

SH-SY5Y cells were propagated in a 1:1 mixture of Eagle's Minimum Essential Medium and Ham's F12 medium supplemented with 10% Fetal Bovine Serum, Penicillin (100 units/ml)/Streptomycin (100 mg/ml) and 2 mM L-Glutamine. The flasks were incubated at 37° C. (5% CO2). Media was changed every 4-6 days until the cells were confluent. On confluency, cells were treated with 25-200 mM homocysteine for 3 hours. After 3 hrs, the cells were harvested using cold PBS, centrifuged, resuspended in SDS sample buffer, and loaded on a 12.5% percent SDS-PAGE gel. Gels were run at 200 V, transferred onto PVDF membrane at 100 V for 1 hr.

Each membrane was blocked for 1 hr in 5% milk, followed by an hour incubation in antibodies, 6A3 (1:50) and 4D9 (1:25) which recognize total and methylated PP2A, respectively. The membranes were then washed 5× for 5 mins each with TBS containing tween (TBST) and then incubated with goat anti-mouse IgG horseradish peroxidase coupled secondary antibody, diluted 1:25,000 in 5% milk prepared in TBS, for 1 hr. Following the secondary antibody incubation, the membranes were washed 5× for 10 mins in TBST and developed with ECL plus (Amersham). Signal intensities of X-ray film exposures for each membrane were quantified by scanning densitometry using NIH Image.

Example 10

Inhibition of PP2A Methylation by Homocysteine

Inhibition of PP2A methylation by homocysteine was determined in cultured cells. Total PP2A and methylated PP2A was determined by western blotting in SH-SY5Y neuroblastoma cells. Homocysteine was added to confluent SH-SY5Y cells to concentrations of 0, 25, 50, 100, and 200 pm. Three hours after adding homocysteine the cells were harvested into cold PBS, mixed with SDS sample buffer, and then analyzed by SDS-PAGE and western blotting. To determine total PP2A, the blots were probed with monoclonal antibody 6A3, which recognizes total PP2A. To determine methylated PP2A the blots were probed with monoclonal antibody 4D9, which recognizes methylated but not unmethylated PP2A. Total PP2A remained much the same at all levels of homocysteine, whereas the level of methylated PP2A declined dramatically with increasing homocysteine concentration.

Example 11

Determination of Tau Phosphorylation

Mice brains were homogenized in 10 times volume/weight buffer containing:

62.5 mM Tris-HCl, pH 6.8, 10% (w/v) glycerol, 5% (v/v) [3-mercaptoethanol, 2.3% (w/v) SDS, 100 nM okadaic acid (OA), 1 mM phenylmethylsulfonyl fluoride, and 1 mM EDTA. This is a modified version of the buffer reported by Planel et al. [Planel, 2001 #54]. The homogenates were boiled for 5 mins and then centrifuged for 15 mins at 4° C. in a Fisher micro-centrifuge model 235A. The supernatant was then diluted 1:2 in SDS-sample buffer and loaded on a 12.5% percent SDS-PAGE gel. Gels were run at 200 V, transferred onto PVDF membrane at 100 V for 1 hr. Each membrane was blocked for 1 hr in 5% milk, followed by overnight incubation in antibodies, CP13 (1:200) and PHF1 (1:500) which recognize phosphoserine 202 and phosphoserine 396/404 respectively [Greenberg, 1992 #55; Otvos, 1994 #59] and TG5 (1:1000), which recognizes a phosphorylation independent epitope on tau [Jicha, 1997 #56]. The following day, membranes were washed 5× for 5 mins each with TBS containing tween (TBST) and then incubated with goat anti-mouse IgG horseradish peroxidase coupled secondary antibody, diluted 1:25,000 in 5% milk prepared in TBS, for 1 hr. Following the secondary antibody incubation, the membranes were washed 5× for 10 mins in TBST and developed with ECL plus (Amersham). Signal intensities of X-ray film exposures for each membrane were quantified by scanning densitometry using NIH Image.

Example 12

Effects of Vitamin Deficiency on Tau Phosphorylation

Phospho-tau is primarily dephosphorylated by a heterotrimeric phosphoprotein phosphatase 2a variant, ABaC. The assembly of ABaC depends on carboxylmethylation of the catalytic subunit (C). Lowered levels of PP2A methylation thus should lead to lowered rates of phospho-tau dephosphorylation. Moreover, the protein kinases that are responsible for tau phosphorylation are themselves activated by phosphorylation. Heterotrimeric, methylated forms of PP2A catalyze the dephosphorylation and inactivation of these kinases. Under conditions where PP2A is disabled because of a methylation deficiency, the kinases would tend to be activated, which would further contribute to tau hyperphosphorylation. This is demonstrated using the mouse diet model described below.

Mice were fed on diets containing or deficient in folate, vitamin B6, and vitamin B12 as described above. Tau phosphorylation was determined in the mice by SDS-PAGE and western blotting using the procedures described above. The western blots were probed using three different tau-specific monoclonal antibodies, as discussed above. As shown in the data below, the total amount of tau, determined by Western blots probed with TG5 antibody, was essentially the same for all the diets. Tau phosphorylation, however, was significantly greater in mice fed diets deficient in folate, B12, and B6 then in mice fed diets containing these vitamins in normal amounts.

Tau Hyperphosphorylation in Mice on Diets Deficient in Folate, B12, and 86

Date from representative Western blots of extracts prepared from mice raised on normal diets (A and B) and vitamin-deficient diets and D). CP13 and PHF1 are monoclonal antibodies specific for phosphorylated tau epitopes. TG5 is a monoclonal specific for Tau independent of its phosphorylation state. Blots were treated as self-contained data sets.

Relative Tau(Vitamin deficient/Antibody Normal diet)

Relative Tau—the fold-induction in the signal relative to the mouse fed standard rodent chow (A diet)—was calculated for each blot, using the program NIH image. Each value is the average of 8 determinations, and the ±value is the standard error of the average.

Example 13

Effect of Methionine Enrichment on Tau Phosphorylation

The effects of methionine enrichment were determined either in the presence or absence of a deficiency for folate, vitamin B6, and vitamin B12. When excess methionine was added to the normal diet, an approximately two-fold increase in plasma Hcy was observed while other variables showed little difference. In contrast, excess methionine added to vitamin-deficient diets did not have a sizeable significant effect on tau hyperphosphorylation and methylation metabolism.

Effects of Methionine Enrichment on Mice Fed Diets with or without Folate, Vitamin B6, and Vitamin B12

Ratios are given for values obtained from mice fed diets enriched with methionine divided by values obtained from mice fed diets not enriched for methionine.

| | Folate, $B_6$, $B_{12}$ | |
|---|---|---|
| | With | Without |
| Hcy | 1.9 | 0.9 |
| SAM | 0.9 | 1.2 |
| SAH | 0.8 | 1.1 |
| CP13 | 1.1 | 1 |
| PHF1 | 1.2 | 0.9 |
| TG5 | 1.2 | 1 |
| Body | 0.9 | 0.9 |
| Brain | 1 | 1 |
| Heart | 0.9 | 0.8 |

Feeding and assays were performed as described above. Hcy, total plasma homocysteine; SAM and SAH values measured in brain homogenates. CP13 and PHF1, tau phosphorylation and TG5, total tau (see data below) body, brain, and heart weights (see data in examples above).

Example 14

Increased PP2A Methylation Prevents or Ameliorates Vascular Inflammation and CAD Development in Hypercysteinemic Mice In one example, mice are placed on diets that results in hypercysteinemia, and allowed to become hypercysteinemic, as described by Hofmann et al. (March 2001), Hypercysteinemia enhances vascular inflammation and accelerates atherosclerosis in a murine model, J. Clin. Invest. 107(6): 675-683, which is incorporated herein by reference in parts pertinent to hypercysteinemia in the murine model and its use in assay and/or discovery and/or development of agents and/or methods and/or treatment regimens and the like to prevent, treat, ameliorate, retard, reverse or cure disease in accordance with the invention herein disclosed, inter alia.

An agent that increases PP2A methylation and PP2A phosphatase activity is administered to a group of the hypercysteinemic mice. A placebo is administered to another group of the same mice. The group receiving the placebo exhibits significantly greater vascular inflammation and accelerated development of atherosclerosis, much as reported by Hofman et al. (March 2001). The group receiving the agent does not exhibit significantly greater vascular inflammation and does not show the same accelerated development of atherosclerosis. The effect of the agent is seen in several experiments with different groups of mice and is dose dependent.

Example 15

Mouse In Vivo PP2A Methylation Assays

Drug leads that test positive in the above screens are tested for efficacy in a mouse model for Alzheimer's. Briefly, mice are either fed a diet that contains the drug or the drug is administered by intra peritoneal injection, and effects on levels of PP2A methylation are assayed in brain using monoclonal antibodies that are specific for methylated PP2A (see above). In parallel with these studies we look for effects of altered levels of PP2A methylation on levels of phosphorylation of specific target proteins using monoclonal antibodies specific for epitopes that contain phosphorylation sites of interest. Drugs that have a beneficial effect on methylation and/or phosphorylation and on the subject mice are selected for additional studies.

Example 16

Increased PP2A Methylation Decreases Tau Hyperphosphorylation in a Mouse AD Model An agent that increases PP2A methylation and PP2A phosphatase activity is administered to groups of mice with hyperphosphorylated tau protein in a model of AD disease, including early onset. Other groups of the same mice are not treated, treated with placebo in the same way, or are treated with other agents that do not affect PP2A or related enzymes or factors. Each group of mice that is treated with the agent exhibits slowed increase of hyperphosphorylated tau, at least, and tau phosphorylation is seem to decrease in most of the mice, in some cases to normal levels. None of the mice receiving the agent before last stage AD, show further signs of AD development through the end of the experiment. Mice in the control groups, in contrast, show increasing tau phosphorylation and eventually develop the progressively more severe symptoms characteristic of these mouse AD models.

Example 17

MAP Kinase Hyperphosphorylation in a Mouse AD Model

Hyperphosphorylation of MAP kinase proteins has been associated with neoplastic transformation. We screen for agents that prevent elevated levels of MAP kinase phosphorylation in the tissue culture and mouse screens (as described above). Agents that prevent the elevated levels of MAP kinase phosphorylation that are induced by elevated total plasma homocysteine are validated candidates for pharmaceuticals to treat or prevent cancer.

Example 18

Better Levels of PPMS in Genetically Deficient Mice

Mice genetically deficient in methylation metabolism and that, as a result, suffer from deleterious PPMS, are kept on a normal diet. A placebo is administered to one group of the mice. An agent that increases PP2A methylation and PP2A phosphatase activity is administered to another group. Administration of the placebo and the agent is the same for each group except for the presence of the agent in the composition administered to one group and not the other. PPMS is determined for mice in each of the groups and the results are compared. Compared with mice receiving the placebo, mice that receive the agent exhibit higher levels of PP2A methylation, higher levels of PP2A phosphatase activity, and healthier levels of PPMS.

Example 19

Combinatorial Library and HTS Screen—Okadaic Acid Scaffolds

Okadaic acid is a potent inhibitor of both PP2A phosphatase activity and methylation of PP2A. Moieties are identified in the compound that (1) most resemble structures likely to inhibit the phosphatase activity of PP2A and (2) most resemble structures likely to inhibit PP2A methylation. Putative methylation structures as described in (2) above, are evaluated and ranked as to such considerations as the following: likelihood of inhibitory effect; likely strength thereof; resemblance to other bioactive compounds and likelihood of unwanted effect; suitability as scaffold for combinatorial synthesis; yield of likely inhibitory candidates if used as combinatorial scaffold; ease of carrying out the syntheses necessary to obtain substantially the estimated yield; and compound diversity yield space for each scaffold; among others.

Based on the foregoing criteria, one or more Okadaic acid-derived scaffolds are obtained and used for syntheses of a two-million compound library of derivatives to be screened as methyltransferase and methylesterase inhibitors and agonists.

The compounds are screened in mixtures or individually in an HTS assay much as described above. All mixtures showing positive results are sub-divided and retested. The division and retesting is repeated for each sample giving a positive result, until as many of the active candidates are singularly purified and then identified by MS (MALDI-TOF, for instance). After retesting, a larger batch of each positive is prepared and then tested as described above for activity in inhibiting or enhancing: PP2A phosphatase activity, methylation of PP2A, PP2A MTase activity, and PP2A MEase activity. The candidates also are tested for deleterious effects on cells in culture. Finally, the best candidates are tested in a mouse model of AD as described above for all of the foregoing and for effect on tau hyperphosphorylation.

REFERENCES

The following references, keyed to the text numbers above, are herein incorporated by reference in their entireties in parts pertinent to the aspects, embodiments, and practice of the invention herein disclosed, particularly in parts pertinent to dietary and other disease models, to PP2A and its activities, to methylation of PP2A, to assay and determination of phosphoprotein phosphorylation, to drug discovery and assay relating to PP2A and other dephosphorylation enzymes, and to methylation and demethylation enzymes active on the same, particularly those that modify PP2A activities, to agents and their formulation regarding the same, and to administration and treatment modalities affecting the same, as disclosed elsewhere herein, among other things.

[1] Seshadri, S., Beiser, A., Selhub, J., Jacques, P. F., Rosenberg, I. H., D'Agostino, R. B., Wilson, P. W. and Wolf, P. A. (2002), N Engl J Med 346, 476-83.
[2] Selkoe, D. J. (2001), Physiol Rev 81, 741-66.
[3] Buee, L., Bussiere, T., Buee-Scherrer, V., Delacourte, A. and Hof, P. R. (2000), Brain Res Brain Res Rev 33, 95-130.
[4] Goldstein, L. S. and Yang, Z. (2000), Annu Rev Neurosci 23, 39-71.
[5] Alonso, A., Zaidi, T., Novak, M., Grundke-lqbal, I. and Iqbal, K. (2001), Proc Nat, Acad Sci USA 98, 6923-8.
[6] Lee, V. M., Goedert, M. and Trojanowski, J. Q. (2001), Annu Rev Neurosci 24, 1121-59.
[7] Bramblett, G. T., Goedert, M., Jakes, R., Merrick, S. E., Trojanowski, J. Q. and Lee, V. M. (1993), Neuron 10, 1089-99.
[8] Biernat, J., Gustke, N., Drewes, G., Mandelkow, E. M. and Mandelkow, E. (1993), Neuron 11, 153-63.
[9] Alonso, A. C., Zaidi, T., Grundke-lqbal, I. and Iqbal, K. (1994), Proc Natl Acad Sci USA 91, 5562-6.
[10] Alonso, A. C., Grundke-lqbal, I. and Iqbal, K. (1996), Nat Med 2, 783-7.
[11] Lewis, J. et al. (2001), Science 293, 1487-91.
[12] Gotz, J., Chen, F., van Dorpe, J. and Nitsch, R. M. (2001), Science 293, 1491-5.
[13] Billingsley, M. L. and Kincaid, R. L. (1997), Biochem J 323, 577-91.
[14] Planet, E., Yasutake, K., Fujita, S. C. and Ishiguro, K. (2001), J Biol Chem 276, 34298-306.
[15] Merrick, S. E., Trojanowski, J. Q. and Lee, V. M. (1997), J Neurosci 17, 5726-37.
[16] Kins, S., Crameri, A., Evans, D. R., Hemmings, B. A., Nitsch, R. M. and Gotz, J. (2001), J Biol Chem 276, 38193-200.
[17] Vogelsberg-Ragaglia, V., Schuck, T., Trojanowski, J. Q. and Lee, V. M. (2001), Exp Neurol 168, 402-12.
[18] Jiang, C. H., Tsien, J. Z., Schultz, P. G. and Hu, Y. (2001), Proc Natl Acad Sci USA 98, 1930-4.
[19] Janssens, V. and Goris, J. (2001), Biochem J 353, 417-39.
[20] Kamibayashi, C., Estes, R., Lickteig, R. L., Yang, Si, Craft, C. and Mumby, M. C. (1994), J Biol Chem 269, 20139-48.
[21] Sontag, E., Nunbhakdi-Craig, V., Bloom, G. S. and Mumby, M. C. (1995), J Cell Biol 128, 1131-44.
[22] Sontag, E., Nunbhakdi-Craig, V., Lee, G., Bloom, G. S. and Mumby, M. C. (1996), Neuron 17, 1201-7.
[23] Sontag, E. et al. (1999), J Biol Chem 274, 25490-8.
[24] Lee, J. and Stock, J. (1993), J Biol Chem 268, 19192-5.
[25] Lee, J., Chen, Y., Tolstykh, T. and Stock, J. (1996), Proc Natl Acad Sci USA 93, 6043-7.
[26] Tolstykh, T., Lee, J., Vafai, S. and Stock, J. B. (2000), Embo J 19, 5682-91.
[27] Wu, J., Tolstykh, T., Lee, J., Boyd, K., Stock, J. B. and Broach, J. R. (2000), Embo J 19, 5672-81.
[28] Yu, X. X. et al. (2001), Mol Biol Cell 12, 185-99.
[29] Wei, H., Ashby, D. G., Moreno, C. S., Ogris, E., Yeong, F. M., Corbett, A. H. and Pallas, D. C. (2001), J Biol Chem 276, 1570-7.
[30] McCaddon, A., Davies, G., Hudson, P., Tandy, S. and Cattell, H. (1998), Int J Geriatr Psychiatry 13, 235-9.
[31] Clarke, R., Smith, A. D., Jobst, K. A., Refsum, H., Sutton, L. and Ueland, P. M. (1998), Arch Neurol 55, 1449-55.
[32] Clarke, R., Daly, L., Robinson, K., Naughten, E., Cahalane, S., Fowler, B. and Graham, I. (1991), N Engl J Med 324, 1149-55.
[33] Boushey, C. J., Beresford, S. A., Omenn, G. S. and Motulsky, A. G. (1995), JAMA 274, 1049-57.
[34] Welch, G. N. and Loscalzo, J. (1998), N Engl J Med 338, 1042-50.
[35] Selhub, J. (1999), Annu Rev Nutr 19, 217-46.
[36] Scott, J. M. and Weir, D. G. (1998), J Cardiovasc Risk 5, 223-7.
[37] Finkelstein, J. D. (1998), Eur J Pediatr 157 Suppl 2, S40-4.
[38] Chiang, P. K., Gordon, R. K., Tal, J., Zang, G. C., Doctor, B. P., Pardhasaradhi, K. and McCann, P. P. (1996), Faseb J 10, 471-80.
[39] Wang, H., Yoshizumi, M., Lai, K., Tsai, J. C., Perrella, M. A., Haber, E. and Lee, M. E. (1997), J Biol Chem 272, 25380-5.
[40] Yi, P., Melnyk, S., Pogribna, M., Pogribny, I. P., Hine, R. J. and James, S. J. (2000), J Biol Chem 275, 29318-23.
[41] Caudill, M. A. et al. (2001), J Nutr 131, 2811-8.
[42] Lucock, M. (2000), Mol Genet Metab 71, 121-38.
[43] Delgado-Reyes, C. V., Wallig, M. A. and Garrow, T. A. (2001), Arch Biochem Biophys 393, 184-186.
[44] Schnyder, G. et al. (2001), N Engl J Med 345, 1593-600.
[45] Selhub, J., Jacques, P. F., Wilson, P. W., Rush, D. and Rosenberg, I. H. (1993), JAMA 270, 2693-8.

[46] Selhub, J., Bagley, L. C., Miller, J. and Rosenberg, I. H. (2000), Am J Clin Nutr 71, 614S-620S.
[47] Grundke-lqbal, I., Igbal, K., Tung, Y. C., Quinlan, M., Wisniewski, H. M., and Binder, L. I. (1986), Abnormal phosphorylation of the microtubule-associated protein Tau (Tau) in Alzheimer cytoskeletal pathology. Proc Natl Acad Sci USA 83: 4913-4917.
[48] Alonso, A. D., Grundke-lqbal, I., Barra, H. S., and Igbal, K. (1997), Abnormal phosphorylation of Tau and the mechanism of Alzheimer neurofibrillary degeneration: sequestration of microtubule-associated proteins 1 and 2 and the disassembly of microtubules by the abnormal Tau. Proc Natl Acad Sci USA 94: 298-303.
[49] Kopke, E, Tung, Y. C, Shaikh, S, Alonso, A. D, Igbal, K, Grundke-lqbal, I (1993), Microtubule-Associated Protein-Tau-Abnormal Phosphorylation of a Non-Paired Helical Filament Pool in Alzheimer-Disease; J. Biol. Chem. 268 (32):24374-24384.
[50] Gong, C. X., Grundke-lqbal, I., Damuni, Z., Igbal, K. (1994), Dephosphorylation of microtubule-associated protein tau by protein phosphatase-1 and -2C and its implication in Alzheimer disease; FEBS Letters. 341(1):94-8.
[51] Chen et al. (2001), Hum Mol Genet 10:433-443.
[52] Gospe et al. (1995), Physiol Behav 58: 935-941.
[53] Cantoni et al. (1978), pp. 155-164 in TRANSMETHYLATION, Usdin et al., Eds., Elaevier, New York.
[54] Planel et al. (2001), J Biol Chem 276: 34298-34306.
[55] Greenberg et al. (1992), J Biol Chem 267: 564-569.
[56] Jicha et al. (1997), J Neurosci Res 48: 128-132.
[57] Bender et al. (1990), Br J Nutr 63: 27-36.
[58] Ha et al. (1984), J Nutr 114:938-948.
[59] Otvos et al. (1994), J Neurosci Res 39: 669-673.

What is claimed is:

1. A method for identifying agents that modulate PP2A methylation, the method comprising steps of:
providing a plurality of candidate test agents;
assessing effects of individual candidate test agents on PP2A methylation status in a PP2A methylation assay that contains PP2A, a PP2A methylase enzyme, and a PP2A demethylase enzyme; and
identifying, based on the assessed effects, one or more test agents that modulate PP2A methylation.

2. The method of claim 1, wherein the step of assessing comprises assessing phosphorylation of a PP2A substrate included in the assay, which substrate is tau.

3. The method of claim 2, wherein tau is hyperphosphorylated in the assay without test agent, and wherein the one or more test agents increase methylation of PP2A and decrease tau hyperphosphorylation.

4. The method of claim 1, wherein the PP2A methylation assay determines activity of a PP2A methylase enzyme or PP2A demethylase enzyme.

5. The method of claim 4, wherein the activity is binding to PP2A.

6. The method of claim 1, wherein the one or more test phosphatase activity of PP2A through their effects on PP2A methylation.

7. The method of claim 1, wherein the one or more test agents increase PP2A methylation.

8. The method of claim 1, wherein the one or more test agents activate the PP2A methylase enzyme.

9. The method of claim 1, wherein the one or more test agents activate the PP2A methylase enzyme, the PP2A demethylase enzyme, or both the PP2A methylase enzyme and the PP2A demethylase enzyme.

10. The method of claim 9, wherein the one or more test agents do not activate the PP2A demethylase enzyme.

11. The method of claim 9, wherein the PP2A methylation status results from effects of the one or more test agents on the PP2A methylase enzyme and the PP2A demethylase enzyme.

12. The method of claim 1, wherein the one or more test agents inhibit the PP2A demethylase enzyme.

13. The method of claim 1, wherein the one or more test agents inhibit the PP2A methylase enzyme, the PP2A demethylase enzyme, or both the PP2A methylase enzyme and the PP2A demethylase enzyme.

14. The method of claim 13, wherein the one or more test agents do not inhibit the PP2A methylase enzyme.

15. The method of claim 13, wherein the PP2A methylation status results from effects of the one or more test agents on the PP2A methylase enzyme and the PP2A demethylase enzyme.

16. The method of claim 1, wherein the one or more test agents interfere with PP2A subunit assembly.

17. The method of claim 16, wherein the one or more test agents interfere with binding of the methylase, the demethylase enzyme, or both the methylase and the demethylase enzyme to PP2A.

18. The method of claim 1, wherein one or more of the PP2A, the methylase enzyme, and the demethylase enzyme is purified.

19. The method of claim 1, wherein one or more of the PP2A, the methylase enzyme, and the demethylase enzyme is provided in the form of a partially purified extract.

20. The method of claim 1, wherein one or more of the PP2A, the methylase enzyme, and the demethylase enzyme is expressed in a cell.

21. The method of claim 1, wherein one or more of the PP2A, the methylase enzyme, and the demethylase enzyme is provided in the form of a mouse that produces one or more of the PP2A, the methylase enzyme, and the demethylase enzyme.

22. The method of claim 1, wherein one or more of the PP2A, the methylase enzyme, and the demethylase enzyme is provided in the form of a human that produces one or more of the PP2A, the methylase enzyme, and the demethylase enzyme.

23. The method of claim 1, wherein the step of assessing comprises contacting the test agents with cells that express one or more of the PP2A, the methylase enzyme, and the demethylase enzyme.

24. The method of claim 23, wherein the step of is followed by a step of determining the PP2A methylation status with the test agents relative to the PP2A methylation status without the test agents.

25. The method of claim 24, wherein the PP2A methylation status refers to an increase in PP2A methylation with the test agents relative to the PP2A methylation status without the test agents.

26. The method of claim 24, wherein the PP2A methylation status refers to a decrease in PP2A methylation with the test agents relative to the PP2A methylation status without the test agents.

27. The method of claim 23, wherein the step of contacting is followed by a step of determining phosphorylation status of at least one substrate of PP2A.

28. The method of claim 27, wherein the at least one substrate of PP2A is tau or MAP kinase.

29. The method of claim 27, wherein the step of determining phosphorylation status refers to detecting an increase in PP2A phosphorylation.

30. The method of claim 27, wherein the step of determining phosphorylation status refers to detecting a decrease in PP2A phosphorylation.

31. The method of claim 1, wherein the step of assessing comprises administering the test agents to an organism that produces one or more of the PP2A, the methylase enzyme, and the demethylase enzyme.

32. The method of claim 31, wherein the step of administering is followed by a step of determining the PP2A methylation status with the test agents or the composition relative to the PP2A methylation status without the test agents or the composition.

33. The method of claim 32, wherein the step of determining PP2A methylation status refers to detecting an increase in PP2A methylation with the test agents relative to the PP2A methylation status without the test agents.

34. The method of claim 32, wherein the PP2A methylation status refers to a decrease in PP2A methylation with the test agents relative to the PP2A methylation status without the test agents.

35. The method of claim 31, wherein the step of administering is followed by a step of determining the phosphorylation status of at least one substrate of PP2A.

36. The method of claim 35, wherein the at least one substrate of PP2A is tau or MAP kinase.

37. The method of claim 35, wherein the step of determining phosphorylation status refers to detecting an increase in PP2A phosphorylation.

38. The method of claim 35, wherein the step of determining phosphorylation status refers to detecting refers to a decrease in PP2A phosphorylation.

39. A method for identifying a composition that modulates PP2A methylation status, the method comprising steps of:
    providing a composition;
    assessing effects of the composition on PP2A methylation status in a PP2A methylation assay that contains PP2A, a PP2A methylase enzyme, and a PP2A demethylase enzyme; and
    determining, based on the assessed effects, that the composition modulates PP2A methylation status.

40. The method of claim 39, wherein the composition is an extract of a natural product.

41. The method of claim 39, wherein the composition is an extract of a traditional medicine.

42. The method of claim 39, wherein the step of assessing comprises assessing phosphorylation of a PP2A substrate included in the assay, which substrate is tau.

43. The method of claim 42, wherein tau is hyperphosphorylated in the assay without the composition, and wherein the composition increases methylation of PP2A and decreases tau hyperphosphorylation.

44. The method of claim 39, wherein the assessed effects comprise activity of the PP2A methylase enzyme.

45. The method of claim 5, wherein the activity is binding to PP2A.

46. The method of claim 39, wherein the assessed effects comprise activity of the PP2A demethylase enzyme.

47. The method of claim 46, wherein the activity is binding to PP2A.

48. The method of claim 39, wherein the composition affects phosphatase activity of PP2A through its effects on PP2A methylation.

49. The method of claim 39, wherein the composition increases PP2A methylation.

50. The method of claim 39, wherein the composition activates the PP2A methylase enzyme.

51. The method of claim 39, wherein the composition activates the PP2A methylase enzyme, the PP2A demethylase enzyme, or both the PP2A methylase enzyme and the PP2A demethylase enzyme.

52. The method of claim 51, wherein the composition does not activate the PP2A demethylase enzyme.

53. The method of claim 51, wherein the PP2A methylation status results from effects of the composition on the PP2A methylase enzyme and the PP2A demethylase enzyme.

54. The method of claim 39, wherein the composition inhibits the PP2A demethylase enzyme.

55. The method of claim 39, wherein the composition inhibits the PP2A methylase enzyme, the PP2A demethylase enzyme, or both the PP2A methylase enzyme and the PP2A demethylase enzyme.

56. The method of claim 55, wherein the composition does not inhibit the PP2A methylase enzyme.

57. The method of claim 55, wherein the PP2A methylation status results from effects of the composition on the PP2A methylase enzyme and the PP2A demethylase enzyme.

58. The method of claim 39, wherein the composition interferes with PP2A subunit assembly.

59. The method of claim 58, wherein the composition interferes with binding of the methylase, the demethylase enzyme, or both the methylase and the demethylase enzyme to PP2A.

60. The method of claim 39, wherein one or more of the PP2A, the methylase enzyme, and the demethylase enzyme is purified.

61. The method of claim 39, wherein one or more of the PP2A, the methylase enzyme, and the demethylase enzyme is provided in the form of a partially purified extract.

62. The method of claim 39, wherein one or more of the PP2A, the methylase enzyme, and the demethylase enzyme is expressed in a cell.

63. The method of claim 39, wherein one or more of the PP2A, the methylase enzyme, and the demethylase enzyme is provided in the form of a mouse that produces one or more of the PP2A, the methylase enzyme, and the demethylase enzyme.

64. The method of claim 39, wherein one or more of the PP2A, the methylase enzyme, and the demethylase enzyme is provided in the form of a human that produces one or more of the PP2A, the methylase enzyme, and the demethylase enzyme.

65. The method of claim 39, wherein the step of assessing comprises contacting the composition with cells that express one or more of the PP2A, the methylase enzyme, and the demethylase enzyme.

66. The method of claim 65, wherein the step of contacting is followed by a step of determining the PP2A methylation status with the composition relative to the PP2A methylation status without the composition.

67. The method of claim 66, wherein the PP2A methylation status refers to an increase in PP2A methylation with the composition relative to the PP2A methylation status without the composition.

68. The method of claim 66, wherein the PP2A methylation status refers to a decrease in PP2A methylation with the composition relative to the PP2A methylation status without the composition.

69. The method of claim 65, wherein the step of contacting is followed by a step of determining phosphorylation status of at least one substrate of PP2A.

70. The method of claim 69, wherein the at least one substrate of PP2A is tau or MAP kinase.

71. The method of claim 69, wherein the step of determining phosphorylation status refers to detecting an increase in PP2A phosphorylation.

72. The method of claim 69, wherein the step of determining phosphorylation status refers to detecting a decrease in PP2A phosphorylation.

73. The method of claim 39, wherein the step of assessing comprises administering the composition to an organism that produces one or more of the PP2A, the methylase enzyme, and the demethylase enzyme.

74. The method of claim 73, wherein the step of administering is followed by a step of determining the PP2A methylation status with the composition relative to the PP2A methylation status without the composition.

75. The method of claim 74, wherein the step of determining PP2A methylation status refers to detecting an increase in PP2A methylation with the composition relative to the PP2A methylation status without the composition.

76. The method of claim 74, wherein the PP2A methylation status refers to a decrease in PP2A methylation with the composition relative to the PP2A methylation status without the composition.

77. The method of claim 73, wherein the step of administering is followed by a step of determining the phosphorylation status of at least one substrate of PP2A.

78. The method of claim 77, wherein the at least one substrate of PP2A is tau or MAP kinase.

79. The method of claim 77, wherein the step of determining phosphorylation status refers to detecting an increase in PP2A phosphorylation.

80. The method of claim 77, wherein the step of determining phosphorylation status refers to detecting refers to a decrease in PP2A phosphorylation.

81. A method for identifying agents that modulate PP2A methylation, the method comprising steps of:
   providing a plurality of test agents that modulate PP2A methylation status in a PP2A methylation assay that contains PP2A, a PP2A methylase enzyme, and a PP2A demethylase enzyme;
   identifying at least one structural moiety whose presence correlates with modulation of PP2A methylation in the PP2A methylation assay;
   providing at least one candidate test agent that also shares the structural moiety;
   assessing effects of the at least one candidate test agent on PP2A methylation status in an assay that contains PP2A, a PP2A methylase enzyme, and a PP2A demethylase enzyme; and
   identifying, based on the assessed effects, one or more test agents that modulate PP2A methylation.

\* \* \* \* \*

UNITED STATES PATENT AND TRADEMARK OFFICE
CERTIFICATE OF CORRECTION

| | | |
|---|---|---|
| PATENT NO. | : 7,794,965 B2 | Page 1 of 1 |
| APPLICATION NO. | : 10/579369 | |
| DATED | : September 14, 2010 | |
| INVENTOR(S) | : Stock et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Tenth Day of May, 2011

David J. Kappos
*Director of the United States Patent and Trademark Office*